US010844100B2

United States Patent
Shibata et al.

(10) Patent No.: US 10,844,100 B2
(45) Date of Patent: Nov. 24, 2020

(54) MUTANT STRAIN OF FILAMENTOUS FUNGUS AND USE THEREFOR

(71) Applicant: Kao Corporation, Tokyo (JP)

(72) Inventors: Nozomu Shibata, Wakayama (JP); Wataru Ogasawara, Nagaoka (JP); Yosuke Shida, Nagaoka (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 16/321,101

(22) PCT Filed: Aug. 2, 2017

(86) PCT No.: PCT/JP2017/028122
§ 371 (c)(1),
(2) Date: Jan. 28, 2019

(87) PCT Pub. No.: WO2018/025929
PCT Pub. Date: Feb. 8, 2018

(65) Prior Publication Data
US 2019/0169239 A1 Jun. 6, 2019

(30) Foreign Application Priority Data

Aug. 2, 2016 (JP) ................. 2016-152134

(51) Int. Cl.
| | |
|---|---|
| *C07K 14/38* | (2006.01) |
| *C12P 21/02* | (2006.01) |
| *C12P 19/14* | (2006.01) |
| *C12N 15/09* | (2006.01) |
| *C12N 15/67* | (2006.01) |
| *C12N 15/80* | (2006.01) |
| *C12P 21/00* | (2006.01) |
| *C12R 1/645* | (2006.01) |
| *C12R 1/885* | (2006.01) |

(52) U.S. Cl.
CPC .............. *C07K 14/38* (2013.01); *C12N 15/09* (2013.01); *C12N 15/67* (2013.01); *C12N 15/80* (2013.01); *C12P 19/14* (2013.01); *C12P 21/00* (2013.01); *C12P 21/02* (2013.01); *C12R 1/645* (2013.01); *C12R 1/885* (2013.01); *C12Y 302/01004* (2013.01); *C12Y 302/01008* (2013.01)

(58) Field of Classification Search
None
See application file for complete search history.

(56) References Cited

FOREIGN PATENT DOCUMENTS

WO    WO 2014/192647 A1    12/2014

OTHER PUBLICATIONS

International Search Report (ISR) for PCT/JP2017/028122; I.A. fd Aug. 2, 2017, dated Nov. 7, 2017 from the Japan Patent Office, Tokyo, Japan.

International Preliminary Report on Patentability (IPRP), Chapter I of the Patent Cooperation Treaty, including the Written Opinion for PCT/JP2017/028122; I.A. fd Aug. 2, 2017, dated Feb. 5, 2019, by the International Bureau of WIPO, Geneva, Switzerland.
Morikawa, Yasushi, "Enzymes of filamentous fungi and Basidiomycetes," Chapter I in "Baiomasu Bunkai Koso Kenkyu no Saizensen : Seruraze hemiseruraze o chushin to shite" ("Research Frontier of Biomass Degrading Enzymes—Focused on Cellulases and Hemicellulases"), Akihiko Kondo, Yoshihiko Amano and Yutaka Tamara, eds, CMC Publishing Co, Ltd., Tokyo, Japan, (Mar. 2012) pp. 10-19.
Ogasawara, W et al., "Comparative genomic analysis of the Japanese phylogenetic tree of cellulolytic microorganism *Trichoderma reesei* mutants," Kagaku to Seibutsu (Aug. 2012) Japan Society for Biosci, Biotech, and Agrochem, 50(8): 592-599.
Martinez, D et al., "Genome sequencing and analysis of the biomass-degrading fungus *Trichoderma reesei* (syn. *Hypocrea jecorina*)," Nat Biotechnol. May 2008;26(5):553-60. doi: 10.1038/nbt1403. Epub May 4, 2008; and its Corrigendum published at Nat Biotechnol Oct. 2008;26(10):1193.
Oakley, BR et al., "A β-tubulin mutation in Aspergillus nidulans that blocks microtubule function without blocking assembly," Cell. Jun. 1981;24(3):837-45.
Doshi, P. et al., "Two α-tubulin genes of *Aspergillus nidulans* encode divergent proteins," Mol Gen Genet. Jan. 1991;225(1):129-41.
Kirk, KE et al., "The tubB α-tubulin gene is essential for sexual development in *Aspergillus nidulans*," Genes Dev. Nov. 1991;5(11):2014-23.
May, GS, "The highly divergent β-tubulins of *Aspergillus nidulans* are functionally interchangeable," J Cell Biol. Nov. 1989;109(5):2267-74.
Tubulin alpha chain 1 [Trichoderma reesei QM6a], database GenBank, EGR50979, [online], Jul. 25, 2016, [retrieval date Oct. 24, 2017], Internet: <URL: https://www.ncbi.nlm.nih.gov/protein/340520743>.
Tubulin alpha chain 2 [Trichoderma reesei QM6a], database GenBank, EGR5093 5, [online], Jul. 25, 2016, [retrieval date Oct. 24, 2017], Internet: <URL: https://www.ncbi.nlm.nih.gov/protein/340520699>.
Tubulin beta chain 1 [Trichoderma reesei QM6a], database GenBank, EGR50613, [online], Jul. 25, 2016, [retrieval date Oct. 24, 2017], Internet: <URL: https://www.ncbi.nlm.nih.gov/protein/340520377>.
Beta-tubulin 2 [Trichoderma reesei RUT C-30], database GenBank, ETS00404, [online], Mar. 23, 2015, [retrieval date Oct. 24, 2017], Internet: <URL: https://www.ncbi.nlm.nih.gov/protein/572277122>.

(Continued)

*Primary Examiner* — Suzanne M Noakes
(74) *Attorney, Agent, or Firm* — Sterne, Kessler, Goldstein & Fox P.L.L.C.

(57) ABSTRACT

A filamentous fungus mutant strain showing improved secretory protein production and a method of producing a protein using the filamentous fungus are provided. The method of producing a protein comprises a step of culturing a filamentous fungus mutant strain in which a function of tubulin is reduced or lost and collecting a protein from a culture product.

14 Claims, 2 Drawing Sheets
Specification includes a Sequence Listing.

(56) References Cited

OTHER PUBLICATIONS

Tubulin nucleotide-binding domain-like protein [Trichoderma reesei RUT C-30], database GenBank, ETR97034, [online], Mar. 23, 2015, [retrieval date Oct. 24, 2017], Internet: <URL: https://www.ncbi.nlm.nih.gov/protein/572273390>.

Zhao, Z et al., "Molecular evolution and functional divergence of tubulin superfamily in the fungal tree of life," Sci Rep 4, 6746 (2015), Published Oct. 23, 2014, https://doi.org/10.1038/srep06746.

[Figure 1]
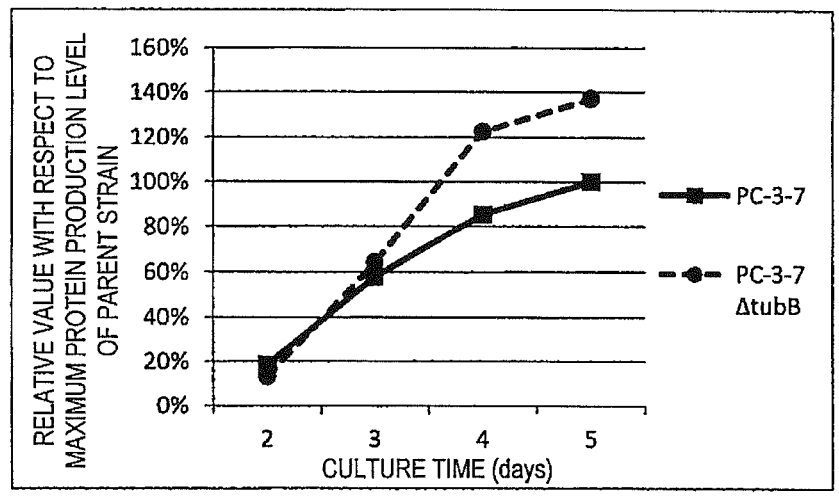
[Figure 2]
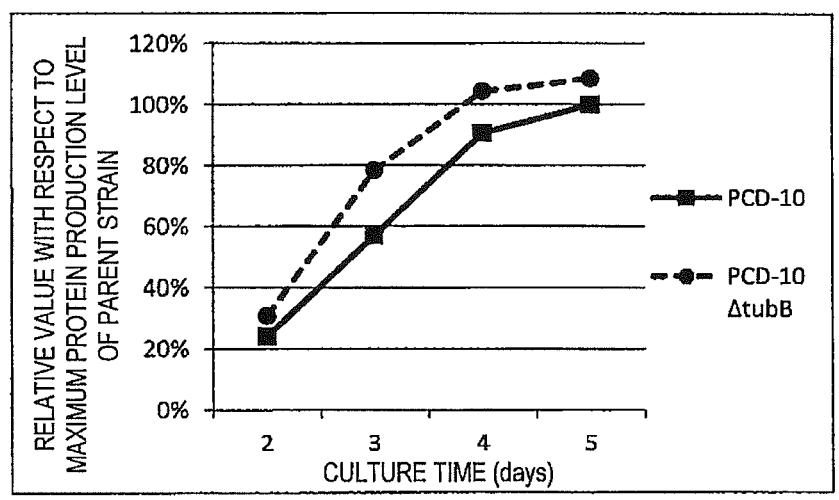

[Figure 3]
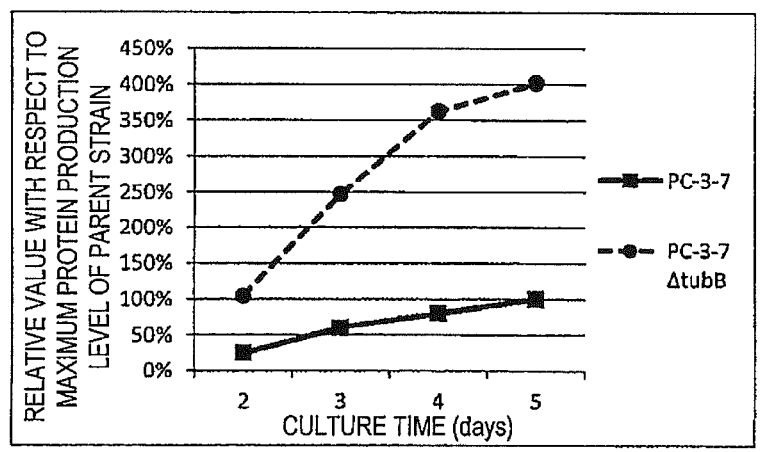
[Figure 4]
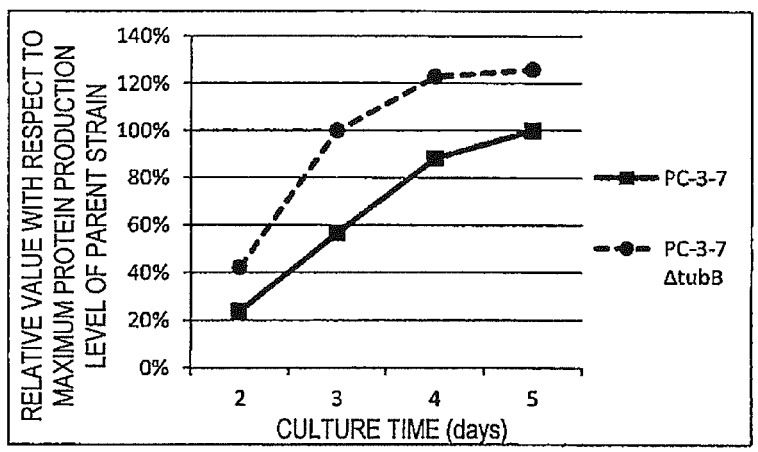

MUTANT STRAIN OF FILAMENTOUS FUNGUS AND USE THEREFOR

FIELD OF THE INVENTION

The present invention relates to a filamentous fungus mutant strain and production of a protein using the filamentous fungus.

BACKGROUND OF THE INVENTION

Filamentous fungi are microorganisms having a high protein-producing ability and producing secretory proteins, such as cellulase, amylase, protease, and lipase, in a culture broth. In general, the culture broth of filamentous fungi contains such multiple proteins, and a protein component having a desired property, such as protease, lipase, or cellulase, is collected from the culture broth and is used industrially.

In recent years, biomass, which is a renewable organic resource from a biological origin, excluding fossil resources has attracted attention. Technologies of producing useful resources, such as alternatives for petroleum resources or biofuel, through production of saccharides by decomposing cellulose and chemical conversion or fermentation using microorganisms of the resulting saccharides are particularly being developed all over the world.

Cellulosic biomass is mainly composed of cellulose, hemicellulose, and lignin, and in order to utilize the biomass, it is necessary to develop a saccharifying enzyme that can highly efficiently decompose cellulose or hemicellulose. In such a case, filamentous fungi such as *Trichoderma* have attracted attention as microorganism that decompose plant polysaccharides and produce various cellulases and xylanases (Non Patent Literature 1). In particular, *Trichoderma* can simultaneously produce cellulase and xylanase and also produces a large amount of a complex enzyme thereof and is therefore useful as a host for cellulase production (Non Patent Literature 2).

Tubulin is a protein forming a microtubule and a centrosome, which are major protein fibers that form a cytoskeleton. As tubulin, three types, $\alpha$-, $\beta$-, and $\gamma$-tubulins, are known. $\alpha$-tubulin and $\beta$-tubulin have similar structures, $\alpha$- and $\beta$-tubulins form a heterodimer, and the heterodimer is polymerized to form a protofilament. Protofilaments are arranged in parallel to form a microtubule. In contrast, $\gamma$-tubulin is known to be responsible for formation of a centrosome.

Tubulin is present in all eukaryotic cells and is highly conserved. It is also known that multiple isoforms are present in a single cell, and the functions thereof differ from each other depending on the locations in the cell. For example, it is known that two $\alpha$-tubulin-like proteins and five $\beta$-tubulin-like proteins are present in *Trichoderma reesei* (Non Patent Literature 3).

In addition, it has been reported that tubulin has various functions in fungi too. For example, it has been reported that nuclear division does not normally occur if benA encoding $\beta$-tubulin is mutated in *Aspergillus nidulans* (Non Patent Literature 4). It also has been reported that gene disruption of tubA encoding $\alpha$-tubulin of *Aspergillus nidulans* inhibits nuclear division (Non Patent Literature 5). Furthermore, it has been reported that deficiency of tubB encoding $\alpha$-tubulin does not affect the growth, but inhibits formation of a diploid nucleus (Non Patent Literature 6). Thus, tubulin is involved in cell division and reproduction also in fungi.

However, it has not been known that a reduction or loss of the function of tubulin is involved in extracellular secretory production of protein.

[Non Patent Literature 1] Akihiko Kondo, Yoshihiko Amano, and Yutaka Tamaru, "Baiomasu Bunkai Koso Kenkyu no Saizensen (Research Frontier of Biomass Decomposing Enzymes—Focused on Cellulases and Hemicellulases—", CMC Publishing Co., Ltd. pp. 10-19

[Non Patent Literature 2] Wataru Ogasawara and Yosuke Shida, "Kagaku to Seibutsu (Chemistry and Biology)", Vol. 50, Japan Society for Bioscience, Biotechnology, and Agrochemistry, Vol. 50, No. 8, pp. 592-599, 2012, August

[Non Patent Literature 3] Martinez, D., et al., 2008, Nature Biotechnology, 26, 553-560

[Non Patent Literature 4] Oakley, B. R., Morris, N. R., 1981, Cell, 24, 837-845

[Non Patent Literature 5] Doshi, P. et al., 1991, Mol. Gen. Genet., 225, 129-141

[Non Patent Literature 6] Kirk, K. E., and Morris, N. R., 1991, Genes Dev., 5, 2014-2023

SUMMARY OF THE INVENTION

The present invention relates to the followings:

[1] A method of producing a protein, the method comprising a step of culturing a filamentous fungus mutant strain in which a function of tubulin is reduced or lost and collecting a protein from a culture product.

[2] A method of improving secretory protein productivity by a filamentous fungus, the method comprising reducing or losing a function of tubulin in a filamentous fungus.

[3] A mutant strain of a *Trichoderma* filamentous fungus wherein a function of tubulin is reduced and lost, wherein secretory protein productivity is improved compared to that of a parent fungal strain.

[4] A method of producing a saccharide from biomass, the method comprising using, as a biomass saccharifying agent, a culture product obtained by culturing a filamentous fungus mutant strain in which a function of tubulin is reduced or lost in the presence of a cellulase inducer.

[5] A method of saccharifying biomass, the method comprising using, as a biomass saccharifying agent, a culture product obtained by culturing a filamentous fungus mutant strain in which a function of tubulin is reduced or lost in the presence of a cellulase inducer.

BRIEF DESCRIPTION OF DRAWINGS

FIG. 1 is a graph showing protein productivity when *Trichoderma reesei* PC-3-7 strain and PC-3-7ΔtubB strain were cultured using crystalline cellulose as a carbon source. The solid line connecting black squares indicates the PC-3-7 strain, and the broken line connecting black circles indicates the PC-3-7ΔtubB strain. The values are relative values with respect to the maximum production amount of PC-3-7 strain assumed as 100%.

FIG. 2 is a graph showing protein productivity when *Trichoderma reesei* PCD-10 strain and PCD-10ΔtubB strain were cultured using crystalline cellulose as a carbon source. The solid line connecting black squares indicates the PCD-10 strain, and the broken line connecting black circles indicates the PCD-10ΔtubB strain. The values are relative values with respect to the maximum production amount of PCD-10 strain assumed as 100%.

FIG. 3 is a graph showing protein productivity when *Trichoderma reesei* PC-3-7 strain and PC-3-7ΔtubB strain were cultured using crystalline cellulose and glucose as carbon sources. The solid line connecting black squares indicates the PC-3-7 strain, and the broken line connecting black circles indicates the PC-3-7ΔtubB strain. The values are relative values with respect to the maximum production amount of PC-3-7 strain assumed as 100%.

FIG. 4 is a graph showing protein productivity when *Trichoderma reesei* PC-3-7 strain and PC-3-7ΔtubB strain were cultured using crystalline cellulose and xylan as carbon sources. The solid line connecting black squares indicates the PC-3-7 strain, and the broken line connecting black circles indicates the PC-3-7ΔtubB strain. The values are relative values with respect to the maximum production amount of the PC-3-7 strain assumed as 100%.

DETAILED DESCRIPTION OF THE INVENTION

The present invention relates to a provision of a filamentous fungus mutant strain showing improved secretory protein production and a method of producing a protein using the filamentous fungus.

The present inventors diligently studied to solve the above-described problems and, as a result, found that secretory protein production is improved in a filamentous fungus mutant strain that has lost the function of tubulin and that efficient protein production is possible by using the fungal strain.

According to the present invention, a filamentous fungus showing improved secretory production of a protein such as cellulase or xylanase is provided, and use of the filamentous fungus allows to produce the protein more efficiently.

In the present specification, amino acid sequence and nucleotide sequence identities are calculated by a Lipman-Pearson method (Lipman, D. J., Pearson, W. R.: Science, 1985, 227: 1435-1441). Specifically, the identity is calculated by performing analysis using a homology analysis (Search homology) program of genetic information processing software Genetyx-Win (Software Development Co.) and setting the unit size to compare (ktup) at 2.

In the present specification, "one or several" used in connection with deletion, substitution, addition, or insertion of amino acid(s) or nucleotide(s) in an amino acid sequence or a nucleotide sequence can be, for example, 1 to 12, preferably 1 to 8, and more preferably 1 to 4, unless otherwise defined. In the present specification, the term "addition" of amino acid(s) or nucleotide(s) includes addition of one or several amino acids or nucleotides to one end or both ends of a sequence.

In the present specification, the team "stringent conditions" relating to hybridization refers to conditions allowing a gene comprising a nucleotide sequence having a sequence identity of about 80% or more or about 90% or more to be verified, unless otherwise defined. Examples of the "stringent conditions" include the conditions described in Molecular Cloning: A LABORATORY MANUAL THIRD EDITION (Joseph Sambrook, David W. Russell, Cold Spring Harbor Laboratory Press, 2001). A person skilled in the art of hybridization can appropriately make stringent conditions by regulating, for example, the salt concentration of a hybridization solution and the temperature, depending on, for example, the nucleotide sequence, the concentration and the length of a probe. In one example, the "stringent conditions" are preferably 5×SSC and 70° C. or more and more preferably 5×SSC and 85° C. or more for hybridization solution; and preferably 1×SSC and 60° C. or more and more preferably 1×SSC and 73° C. or more for washing condition. The combinations of SSC and temperature conditions are merely examples, and a person skilled in the art can achieve appropriate stringency by appropriately combining the above-mentioned factors or other ones determining the stringency of hybridization.

In the present specification, the terms "upstream" and "downstream" of a gene refer to a region extending from the 5' side and the 3' side, respectively, of a targeted gene or region. The upstream and the downstream of a gene are not limited to the upstream region and the downstream region from the translation initiation site of the gene, unless otherwise defined.

<Construction of Filamentous Fungus Mutant Strain>

In the filamentous fungus mutant strain of the present invention, the function of tubulin is reduced or lost.

Tubulin is a protein forming a microtubule and a centrosome, which are major protein fibers that form a cytoskeleton, and as structural proteins of tubulin, three types, α-tubulin, β-tubulin, and γ-tubulin, are known. α-tubulin and β-tubulin have similar structures, α- and β-tubulins form a heterodimer, and the heterodimer is polymerized to form a protofilament. Further, γ-tubulin is known to be responsible for formation of a centrosome.

In the present invention, the term "tubulin" encompasses α-, β-, and γ-tubulins unless especially specified and preferably refers to α- or β-tubulin, and more preferably α-tubulin.

For example, α-tubulin of *Trichoderma reesei* is registered in the NCBI database as Tubulin alpha chain 1 (TRIREDRAFT_120830: SEQ ID NO: 2) and Tubulin alpha chain 2 (TRIREDRAFT_120789: SEQ ID NO: 4); and β-tubulin is registered as Tubulin beta chain 1 (TRIREDRAFT_21742: SEQ ID NO: 6) and Tubulin beta chain 2 (TRIREDRAFT_122886: SEQ ID NO: 8). In addition, Hypothetical protein (TRIREDRAFT_58421: SEQ ID NO: 10), Hypothetical protein (TRIREDRAFT_124181: SEQ ID NO: 12), and WD40 repeat-like protein (TRIREDRAFT_65771: SEQ ID NO: 14) are registered as those including β-tubulin domains.

Examples of α-tubulin of filamentous fungi other than *Trichoderma reesei* include Tubulin alpha-1 chain (NCBI-Protein ID: XP_657920) and Tubulin alpha-2 chain (NCBI-Protein ID: XP_680839) of *Aspergillus nidulans*; tubulin alpha-2 (NCBI-Protein ID: XP_963223) and alpha tubulin (NCBI-Protein ID: XP_958904) of *Neurospora crassa*; and tubulin/FtsZ family protein (NCBI-Protein ID: KKO97118) of *Trichoderma harzianum*. These α-tubulins have amino acid sequence identities of 68% to 89% with the Tubulin alpha chain 1 (TRIREDRAFT_120830) and amino acid sequence identities of 68% to 93% with Tubulin alpha chain 2 (TRIREDRAFT_120789) of *Trichoderma reesei*.

Examples of β-tubulin include TUBULIN BETA-1 CHAIN (NCBI-Protein ID: XP_658786) and TUBULIN BETA-2 CHAIN (NCBI-Protein ID: XP_664442) of *Aspergillus nidulans*; and tubulin beta chain (NCBI-Protein ID: XP_957669) of *Neurospora crassa*. These β-tubulins have amino acid sequence identities of 84% to 91% with Tubulin beta chain 1 (TRIREDRAFT_21742) and amino acid sequence identities of 82% to 91% with Tubulin beta chain 2 (TRIREDRAFT_122886) of *Trichoderma reesei*.

Accordingly, preferred examples of α-tubulin in the present invention include the followings:

(A) a protein having the amino acid sequence represented by SEQ ID NO: 2 or 4;

(B) a protein having an amino acid sequence represented by SEQ ID NO: 2 or 4 in which one or several amino acids are deleted, substituted, added or inserted and having a function as α-tubulin; and (C) a protein having an amino acid sequence with an identity of 80% or more with the amino acid sequence represented by SEQ ID NO: 2 or 4 and having a function as α-tubulin.

Examples of β-tubulin include the followings:

(D) a protein having the amino acid sequence represented by SEQ ID NO: 6, 8, 10, 12, or 14;

(E) a protein having an amino acid sequence represented by SEQ ID NO: 6, 8, 10, 12, or 14 in which one or several amino acids are deleted, substituted, added or inserted and having a function as β-tubulin; and (F) a protein having an amino acid sequence with an identity of 80% or more with the amino acid sequence represented by SEQ ID NO: 6, 8, 10, 12, or 14 and having a function as β-tubulin.

Examples of the amino acid sequence having an identity of 80% or more with the amino acid sequence represented by SEQ ID NO: 2, 4, 6, 8, 10, 12 or 14 include amino acid sequences having an identity of preferably 90% or more, more preferably 95% or more, further preferably 97%, further preferably 98%, and further preferably 99% or more.

Tubulin is a protein forming a microtubule and a centrosome; and α-tubulin and β-tubulin form a heterodimer, which forms a protofilament by polymerization. Protofilaments are arranged in parallel to form a microtubule. A protein having a function as α-tubulin and a protein having a function as β-tubulin in the present invention are proteins having abilities of forming a heterodimer and a protofilament by polymerization, as in α-tubulin and β-tubulin.

In the present invention, the "function of tubulin is reduced or lost" may be that the expression of tubulin is reduced compared to that in the parent strain or lost, preferably that the expression of one or more of α- and β-tubulins is reduced compared to that in the parent strain or lost to inhibit formation of a heterodimer of α- and β-tubulins, and further preferably that the expression of α-tubulin is reduced compared to that in the parent strain or lost to inhibit formation of a heterodimer of α- and β-tubulins.

In the present invention, the "expression" of tubulin means that a translation product is produced from a gene encoding the protein and is localized at the site of action in a functional state. A reduction or loss in the expression of tubulin means a state in which the amount of tubulin present in the filamentous fungus mutant strain cells is significantly reduced compared to that in the parent strain or lost as a result of modification at a genetic level, transcriptional level, posttranscriptional regulation level, translational level, or posttranslational modification level.

The "reduction in the expression of tubulin compared to that in the parent strain" means that the expression amount of tubulin in filamentous fungi is reduced compared to that of the parent strain, more specifically, the expression amount of tubulin in the cells is reduced to usually 50% or less, preferably 20% or less, and more preferably 10% or less compared to that in the parent strain, and thereby the activity is also similarly reduced. It is most preferred that the expression amount of tubulin is 0%, that is, the expression of tubulin is lost.

The comparison of expression amounts of tubulin is performed based on the expression amount of the tubulin protein.

The expression amount of tubulin can be measured by a known immunological method, such as western blotting or immunohistochemical staining.

The filamentous fungus mutant strain in which tubulin expression is reduced compared to a parent strain or is lost preferably can be acquired by deleting or inactivating the tubulin gene on the chromosomal DNA of the filamentous fungus parent strain. Herein, the tubulin gene refers to a DNA having a transcriptional region including an ORF and a transcriptional regulatory region such as a promoter of the gene.

In the present invention, examples of the α-tubulin gene preferably include any of the following:

(a) a polynucleotide having the nucleotide sequence represented by SEQ ID NO: 1 or 3;

(b) a polynucleotide having a nucleotide sequence with an identity of 80% or more, preferably 85% or more, more preferably 90% or more, further preferably 95% or more, further preferably 96% or more, further preferably 97% or more, further preferably 98% or more, and further preferably 99% or more with the nucleotide sequence represented by SEQ ID NO: 1 or 3 and encoding a protein having a function as α-tubulin;

(c) a polynucleotide hybridizing to a complementary strand of the polynucleotide having the nucleotide sequence represented by SEQ ID NO: 1 or 3 under stringent conditions and encoding a protein having a function as α-tubulin;

(d) a polynucleotide encoding a protein having the amino acid sequence represented by SEQ ID NO: 2 or 4;

(e) a polynucleotide encoding a protein having the amino acid sequence represented by SEQ ID NO: 2 or 4 in which one or several amino acids are deleted, substituted, added or inserted and having a function as α-tubulin; and (f) a polynucleotide encoding a protein having an amino acid sequence with an identity of 80% or more, preferably 85% or more, more preferably 90% or more, further preferably 95% or more, further preferably 96% or more, further preferably 97% or more, further preferably 98% or more, and further preferably 99% or more with the amino acid sequence represented by SEQ ID NO: 2 or 4 and having a function as α-tubulin.

Preferred examples of the β-tubulin gene includes the followings:

(g) a polynucleotide having the nucleotide sequence represented by SEQ ID NO: 5, 7, 9, 11, or 13;

(h) a polynucleotide having a nucleotide sequence with an identity of 80% or more, preferably 85% or more, more preferably 90% or more, further preferably 95% or more, further preferably 96% or more, further preferably 97% or more, further preferably 98% or more, and further preferably 99% or more with the nucleotide sequence represented by SEQ ID NO: 5, 7, 9, 11, or 13 and encoding a protein having a function as β-tubulin;

(i) a polynucleotide hybridizing to a complementary strand of the polynucleotide having the nucleotide sequence represented by SEQ ID NO: 5, 7, 9, 11, or 13 under stringent conditions and encoding a protein having a function as β-tubulin;

(j) a polynucleotide encoding a protein having the amino acid sequence represented by SEQ ID NO: 6, 8, 10, 12, or 14;

(k) a polynucleotide encoding a protein having the amino acid sequence represented by SEQ ID NO: 6, 8, 10, 12, or 14 in which one or several amino acids are deleted, substituted, added or inserted and having a function as β-tubulin; and (l) a polynucleotide encoding a protein having an amino acid sequence with an identity of 80% or more, preferably 85% or more, more preferably 90% or more, further preferably 95% or more, further preferably 96% or more, further preferably 97% or more, further preferably 98% or more, and further preferably 99% or more with the amino acid sequence represented by SEQ ID NO: 6, 8, 10, 12, or 14 and having a function as β-tubulin.

Examples of deletion or inactivation of the tubulin gene include introduction of a mutation into one or more nucleotides on the nucleotide sequence of the gene, that is, deletion of a part or the whole of the nucleotide sequence of the gene, or substitution for or insertion to the nucleotide sequence of another nucleotide sequence (in this case, the amino acid sequence of tubulin may be the same as or different from that of a parent strain).

Examples of the nucleotide region into which a mutation is introduced include a transcriptional region of the tubulin gene and transcriptional regulatory region, such as a promoter and an enhancer (transcriptional activation region), of the gene, and preferred is the transcriptional region.

Examples of the transcriptional regulatory region of the tubulin gene include a region of 30 nucleotides upstream of the 5' end of the transcriptional region of the tubulin gene on the chromosomal DNA. Examples of the transcriptional activation region of the tubulin gene include a region corresponding to the nucleotides −1000 to −500 upstream of the gene.

A nucleotide mutation may be introduced into the transcriptional region with any limitation of the kind or the number of nucleotides as long as it can reduce or lose the tubulin expression. Examples of deletion of nucleotides include deletion of a part of the transcriptional region, preferably 10 nucleotides or more, more preferably 20 nucleotides or more, further preferably 100 nucleotides or more, and further preferably 200 nucleotides or more, and further preferably deletion of the whole of the transcriptional region. Examples of substitution of nucleotides include substitution of nucleotides within a range from the 5' end of the transcriptional region to the 150th nucleotide, preferably to the 100th nucleotide, more preferably to the 50th nucleotide, further preferably to the 30th nucleotide, and further preferably to the 20th nucleotide with a nonsense codon. Examples of insertion of nucleotides include addition of 50 or more nucleotides, preferably 100 or more nucleotides, more preferably 200 or more nucleotides, further preferably 500 or more nucleotides, and further preferably 1 kb or more of a DNA fragment at the position following the nucleotides within a range from the 5' end of the transcriptional region to the 150th nucleotide, preferably to the 100th nucleotide, more preferably to the 50th nucleotide, further preferably to the 30th nucleotide, and further preferably to the 20th nucleotide. Preferred examples of the form of the addition of nucleotides include introduction of a drug resistance gene such as a hygromycin resistance gene and an aureobasidin resistance gene, or an auxotrophic gene such as an acetamidase gene that is not possessed by the filamentous fungi.

The method of introducing a nucleotide mutation into the tubulin gene on the chromosomal DNA of filamentous fungi may be, for example, a method of using homologous recombination. In a method of using common homologous recombination, for example, a gene mutated by deletion, substitution, or insertion of nucleotides is inserted between the upstream region and the downstream region of the tubulin gene to produce a DNA fragment including a drug resistance gene or an auxotrophic gene, and the DNA fragment is used to cause homologous recombination in the locus of the tubulin gene in a host cell to which nucleotide deletion or the like is desired to be introduced.

In the method using homologous recombination, specifically, i) the DNA fragment for homologous recombination is introduced into a filamentous fungus parent strain by a usual manner, and subsequently a transformant into which, as a result of homologous recombination, a plasmid for homologous recombination has been introduced on the chromosomal DNA is selected using drug resistance or auxotrophy as an index; ii) PCR is performed using the chromosomal DNA of the resulting transformant as a template. The primers on this occasion are designed such that the site where the nucleotides of the gene are deleted, substituted, or inserted is amplified. A strain in which a gene having the original length is not amplified, but a gene having a length reflecting the deletion, substitution, or insertion of the nucleotides is amplified is selected; and iii) finally, a strain in which the mutated gene is introduced into only the locus of the chromosomal DNA and not introduced into another site can be obtained by Southern analysis.

Alternatively, a nucleotide mutation may be introduced into the tubulin gene on the chromosomal DNA of a parent strain by, for example, a method using a bacteriophage or conjugation.

The filamentous fungus mutant strain of the present invention can also be obtained by subjecting a filamentous fungus parent strain to mutation processing and then selecting a strain in which the tubulin expression is reduced compared to the parent strain or is lost. Examples of the mutation processing include treatment with N-methyl-N'-nitro-N-nitrosoguanidine (NTG), ethylnitrosourea, or ultraviolet light (Shinban Biseibutsu Zikken-ho (New Edition, Microorganisms Experimental Methods), 1999, pp. 126-134, Kodansha Scientific Ltd.), and irradiation with radioactive rays. In addition, a variety of alkylating agents and carcinogens can be used as mutagens.

Alternatively, the tubulin expression can be reduced without introducing a mutation into the tubulin gene. Examples of such a method include introduction of a nucleic acid having an activity of degrading a transcriptional product of a gene encoding a protein or a nucleic acid suppressing translation of the transcriptional product into a protein. Examples of such a nucleic acid include a nucleic acid having a nucleotide sequence complementary or substantially complementary to the nucleotide sequence of mRNA encoding the protein or a part of the nucleotide sequence.

A nucleotide sequence substantially complementary to the nucleotide sequence of mRNA encoding tubulin refers to a nucleotide sequence having complementarity such that the nucleotide sequence binds to the target sequence of the mRNA to inhibit the translation thereof under physiological conditions inside the target filamentous fungus cells, and specifically, for example, a nucleotide sequence having an identity of about 80% or more, preferably about 90% or more, more preferably about 95% or more, and further preferably about 97% or more with the nucleotide sequence completely complementary to the nucleotide sequence of the mRNA (i.e., the nucleotide sequence of a complementary strand of the mRNA) in the overlapping region.

More specifically, examples of the nucleotide sequence complementary or substantially complementary to the nucleotide sequence of mRNA encoding tubulin include polynucleotides in the above-described (a) to (l).

Preferred examples of the mRNA encoding tubulin include mRNA encoding α-tubulin or β-tubulin of *Trichoderma reesei* having the nucleotide sequence represented by SEQ ID NO: 1, 3, 5, 7, 9, 11 or 13.

"A part of the nucleotide sequence complementary or substantially complementary to the nucleotide sequence of mRNA encoding tubulin" may have no limitation of length and position as long as it can specifically binds to the mRNA of tubulin and can inhibit the translation of the mRNA into the protein. From the viewpoint of sequence specificity, the part complementary or substantially complementary to the target sequence includes at least 10 or more nucleotides, preferably about 15 or more nucleotides, and more preferably about 20 or more nucleotides.

Specifically, preferred examples of the nucleic acid having a nucleotide sequence complementary or substantially complementary to the nucleotide sequence of mRNA encoding tubulin or a part of the nucleotide sequence includes the following (i) to (iii):

(i) Antisense RNA to mRNA encoding tubulin;
(ii) Small interfering RNA (siRNA) to mRNA encoding tubulin; and
(iii) Ribozyme to mRNA encoding tubulin.

The parent strain in the present invention may be any filamentous fungi that express tubulin, and examples thereof include filamentous fungi belonging to Eumycota or Oomycota. Specifically, the filamentous fungi are, for example, those belonging to *Trichoderma, Aspergillus, Penicillium, Neurospora, Fusarium, Chrysosporium, Humicola, Emericella, Hypocrea, Acremonium, Chrysosporium, Myceliophthora, Piromyces, Talaromyces*, or *Thielavia*. The filamentous fungi are preferably those belonging to *Trichoderma*.

Examples of the filamentous fungi belonging to *Trichoderma* include *Trichoderma reesei, Trichoderma longibrachiatum, Trichoderma harzianum, Trichoderma koningii*, and *Trichoderma viride*. The filamentous fungi are preferably *Trichoderma reesei* and more preferably *Trichoderma reesei* PCD-10 strain (FERN P-8172) and *Trichoderma reesei* PC-3-7 strain (ATCC66589).

The filamentous fungi as the parent strain may be a wild-type strain, a strain artificially bred from the wild-type strain, or a variant strain (variant) or a mutant in which a nucleotide sequence in the genome is substituted, added, deleted, or modified.

Preferred examples of the filamentous fungus mutant strain of the present invention include filamentous fungi obtained by deleting the α-tubulin gene of the *Trichoderma reesei* PCD-10 strain or the *Trichoderma reesei* PC-3-7 strain by homologous recombination to lose the α-tubulin expression. Specifically, PC-3-7ΔtubB strain and PCD-10ΔtubB strain disclosed in Example described below are examples.

In the thus-constructed filamentous fungus mutant strain of the present invention, the function of tubulin in the cells is reduced or lost, and the secretory protein productivity is consequently improved compared to that of the parent strain. In addition, inhibition of the production of cellulase by glucose is suppressed compared to that in the parent strain, and even if a high concentration of glucose is present in the culture medium, a reduction in the productivity of cellulase is suppressed.

<Production of Protein>

A protein can be generated and accumulated in a culture broth by culturing the filamentous fungus mutant strain of the present invention, and the protein can be produced by collecting the protein from the culture product. Since filamentous fungi generate multiple proteins in a culture broth, the protein produced by the present invention may be a mixture of multiple proteins.

Here, examples of the protein include cellulase, xylanase, protease, lipase, exoglucanase, endoglucanase, β-glucosidase, mannase, arabinase, arabinofuranosidase, galactase and amylase.

For example, when cellulase or xylanase is produced, the filamentous fungus mutant strain of the present invention is cultured in the presence of a cellulase inducer, such as cellulose, sophorose, or a cellooligosaccharide (e.g., cellobiose, cellotriose, cellotetraose, cellopentaose, or cellohexaose), and cellulase or xylanase is collected from the culture product.

The protein produced by the present invention may be a heterologous protein that is not secretion produced by filamentous fungi originally. In such a case, proteins including a heterologous protein can be obtained by inserting a gene encoding the heterologous protein into the filamentous fungus mutant strain of the present invention to produce a recombinant filamentous fungus and culturing the recombinant filamentous fungus. Furthermore, in order to improve the efficiency of secretory production, it is also possible to modify a gene encoding a desired protein. Specifically, the modification is to modify a gene such that a secretory signal peptide is functionally added to the desired protein. The secretory signal peptide is desirably added to the amino terminus of the desired protein. The addition of the secretory signal peptide can improve the secretory productivity.

The culture medium used for the production of proteins may be a synthetic culture medium or a natural culture medium that contains nutrients necessary for proliferation of the filamentous fungi of the present invention and production of various proteins, such as a carbon source, a nitrogen source, inorganic salts, and vitamins.

The carbon source may be any carbon source that can be assimilated by the filamentous fungus mutant strain of the present invention, and examples thereof include carbohydrates such as glucose and fructose; alcohols such as ethanol and glycerol; and organic acids such as acetic acid, in addition to the above-mentioned cellulase inducers. These carbon sources may be used alone or in combination of two or more thereof.

Examples of the nitrogen source include ammonia; ammonium salts such as ammonium sulfate; nitrogen compounds such as amine; natural nitrogen sources such as peptone and soybean hydrolysates.

Examples of the inorganic salt include potassium phosphate, magnesium sulfate, sodium chloride, ferrous sulfate, and potassium carbonate.

Examples of the vitamin include biotin and thiamine. The medium can further optionally contain a substance required for growth of the filamentous fungi of the present invention.

The culture is preferably performed under aerobic conditions such as shake culture or aerated and agitated culture. The culture temperature is preferably 10° C. or more, more preferably 20° C. or more, and more preferably 25° C. or more; and preferably 50° C. or less, more preferably 42° C. or less, and more preferably 35° C. or less. The temperature is preferably from 10° C. to 50° C., more preferably from 20° C. to 42° C., and more preferably from 25° C. to 35° C.

The pH in the culture is from 3 to 9 and preferably from 4 to 5. The culture time is from 10 hours to 10 days and preferably from 2 to 7 days.

After the completion of the culture, the culture product is collected, is subjected to cell pulverization by, for example, ultrasonic waves or pressurization as needed, and is solid-liquid separated by, for example, filtration or centrifugation, followed by an appropriate combination of ultrafiltration, salting-out, dialysis, chromatography, and so on to obtain a desired protein. The degree of separation and purification is not particularly limited. The culture supernatant or its roughly separated and purified product itself can also be used as a protein.

<Saccharification of Biomass>

A monosaccharide can be produced using the culture product obtained by culturing the filamentous fungus mutant strain of the present invention in the presence of a cellulase inducer, as a biomass saccharifying agent and heating the culture product together with a cellulose- or xylan-containing material (biomass) in an aqueous solvent with stirring or shaking to degrade or saccharify the biomass.

As the cellulose- or xylan-containing material, those exemplified as the cellulase inducers above can be used.

In the degradation or saccharification of biomass, the reaction solution may have any pH and any temperature within ranges that do not inactivate the cellulase or xylanase. Generally, when the reaction is performed at normal pressure, the temperature is within a range of 5° C. to 95° C., and the pH is within a range of 1 to 11.

The process of degradation or saccharification of biomass may be a batch system or a continuous system.

Regarding the above-described embodiments, the present invention further discloses the following aspects:

<1> A method of producing a protein, the method comprising a step of culturing a filamentous fungus mutant strain in which a function of tubulin is reduced or lost and collecting a protein from a culture product;

<2> A method of improving secretory protein productivity of a filamentous fungus, the method comprising reducing or losing a function of tubulin in a filamentous fungus;

<3> The method according to aspect <1> or <2>, wherein the reducing or losing the function of tubulin is reducing or losing an expression of tubulin compared to that in a parent strain;

<4> The method according to any one of aspects <1> to <3>, wherein the tubulin is α-tubulin and/or β-tubulin;

<5> The method according to any one of aspects <1> to <3>, wherein the reducing or losing a function of tubulin is acquired by deleting or inactivating a gene encoding the tubulin;

<6> The method according to aspect <5>, wherein the gene encoding the tubulin is a gene encoding α-tubulin and/or β-tubulin;

<7> The method according to aspect <6>, wherein the gene encoding α-tubulin is represented by any of the following polynucleotides (a) to (f):

(a) a polynucleotide having the nucleotide sequence represented by SEQ ID NO: 1 or 3;

(b) a polynucleotide having a nucleotide sequence with an identity of 80% or more with the nucleotide sequence represented by SEQ ID NO: 1 or 3 and encoding a protein having a function as α-tubulin;

(c) a polynucleotide hybridizing to a complementary strand of the polynucleotide having the nucleotide sequence represented by SEQ ID NO: 1 or 3 under stringent conditions and encoding a protein having a function as α-tubulin;

(d) a polynucleotide encoding a protein having the amino acid sequence represented by SEQ ID NO: 2 or 4;

(e) a polynucleotide encoding a protein having the amino acid sequence represented by SEQ ID NO: 2 or 4 in which one or several amino acids are deleted, substituted, added or inserted and having a function as α-tubulin; and (f) a polynucleotide encoding a protein having an amino acid sequence with an identity of 80% or more with the amino acid sequence represented by SEQ ID NO: 2 or 4 and having a function as α-tubulin;

<8> The method according to aspect <6>, wherein the gene encoding β-tubulin is represented by any of the following polynucleotides (g) to (l):

(g) a polynucleotide having the nucleotide sequence represented by SEQ ID NO: 5, 7, 9, 11, or 13;

(h) a polynucleotide having a nucleotide sequence with an identity of 80% or more with the nucleotide sequence represented by SEQ ID NO: 5, 7, 9, 11, or 13 and encoding a protein having a function as β-tubulin;

(i) a polynucleotide hybridizing to a complementary strand of the polynucleotide having the nucleotide sequence represented by SEQ ID NO: 5, 7, 9, 11, or 13 under stringent conditions and encoding a protein having a function as β-tubulin;

(j) a polynucleotide encoding a protein having the amino acid sequence represented by SEQ ID NO: 6, 8, 10, 12, or 14;

(k) a polynucleotide encoding a protein having the amino acid sequence represented by SEQ ID NO: 6, 8, 10, 12, or 14 in which one or several amino acids are deleted, substituted, added or inserted and having a function as β-tubulin; and (l) a polynucleotide encoding a protein having an amino acid sequence with an identity of 80% or more with the amino acid sequence represented by SEQ ID NO: 6, 8, 10, 12, or 14 and having a function as β-tubulin;

<9> A method according to any one of aspects <1> to <8>, wherein the filamentous fungus is a filamentous fungus belonging to *Acremonium*, *Aspergillus*, *Chrysosporium*, *Fusarium*, *Humicola*, *Myceliophthora*, *Neurospora*, *Penicillium*, *Piromyces*, *Talaromyces*, *Thermoascus*, *Thielavia*, or *Trichoderma*;

<10> The method according to aspect <9>, wherein the filamentous fungus is a *Trichoderma* filamentous fungus;

<11> The method according to aspect <10>, wherein the filamentous fungus is *Trichoderma reesei*;

<12> A mutant strain of a *Trichoderma* filamentous fungus, wherein a function of tubulin is reduced or lost, wherein secretory protein productivity is improved compared to that of a parent fungal strain;

<13> The mutant strain according to aspect <12>, wherein the reduction or loss of a function of tubulin is a reduction or loss of an expression of tubulin compared to that in the parent strain;

<14> The mutant strain according to aspect <12> or <13>, wherein the tubulin is α-tubulin and/or β-tubulin;

<15> The mutant strain according to aspect <12> or <13>, wherein the reduction or loss of the function of tubulin is acquired by deleting or inactivating a gene encoding the tubulin;

<16> The mutant strain according to aspect <15>, wherein the gene encoding the tubulin is a gene encoding α-tubulin and/or β-tubulin;

<17> The mutant strain according to aspect <16>, wherein the gene encoding α-tubulin is represented by any of the following polynucleotides (a) to (f):

(a) a polynucleotide having the nucleotide sequence represented by SEQ ID NO: 1 or 3;

(b) a polynucleotide having a nucleotide sequence with an identity of 80% or more with the nucleotide sequence represented by SEQ ID NO: 1 or 3 and encoding a protein having a function as α-tubulin;

(c) a polynucleotide hybridizing to a complementary strand of the polynucleotide having the nucleotide sequence represented by SEQ ID NO: 1 or 3 under stringent conditions and encoding a protein having a function as α-tubulin;

(d) a polynucleotide encoding a protein having the amino acid sequence represented by SEQ ID NO: 2 or 4;

(e) polynucleotide encoding a protein having the amino acid sequence represented by SEQ ID NO: 2 or 4 in which one or several amino acids are deleted, substituted, added or inserted and having a function as α-tubulin; and (f) a polynucleotide encoding a protein having an amino acid sequence with an identity of 80% or more with the amino acid sequence represented by SEQ ID NO: 2 or 4 and having a function as α-tubulin;

<18> The mutant strain according to aspect <16>, wherein the gene encoding β-tubulin is represented by any of the following polynucleotides (g) to (l):

(g) a polynucleotide having the nucleotide sequence represented by SEQ ID NO: 5, 7, 9, 11, or 13;

(h) a polynucleotide having a nucleotide sequence with an identity of 80% or more with the nucleotide sequence represented by SEQ ID NO: 5, 7, 9, 11, or 13 and encoding a protein having a function as β-tubulin;

(i) a polynucleotide hybridizing to a complementary strand of the polynucleotide having the nucleotide sequence represented by SEQ ID NO: 5, 7, 9, 11, or 13 under stringent conditions and encoding a protein having a function as β-tubulin;

(j) a polynucleotide encoding a protein having the amino acid sequence represented by SEQ ID NO: 6, 8, 10, 12, or 14;

(k) a polynucleotide encoding a protein having the amino acid sequence represented by SEQ ID NO: 6, 8, 10, 12, or 14 in which one or several amino acids are deleted, substituted, added or inserted and having a function as β-tubulin; and (l) a polynucleotide encoding a protein having an amino acid sequence with an identity of 80% or more with the amino acid sequence represented by SEQ ID NO: 6, 8, 10, 12, or 14 and having a function as β-tubulin;

<19> The mutant strain according to any one of aspects <12> to <18>, wherein the filamentous fungus is *Trichoderma reesei*;

<20> A method of producing a saccharide from biomass, the method comprising using, as a biomass saccharifying agent, a culture product obtained by culturing a filamentous fungus mutant strain in which a function of tubulin is reduced or lost in the presence of a cellulase inducer;

<21> A method of saccharifying biomass, the method comprising using, as a biomass saccharifying agent, a culture product obtained by culturing a filamentous fungus mutant strain in which a function of tubulin is reduced or lost in the presence of a cellulase inducer;

<22> The method according to any one of aspects <1> to <11>, wherein the protein is one or more selected from the group consisting of cellulase, xylanase, protease, lipase, exoglucanase, endoglucanase, β-glucosidase, mannase, arabinase, arabinofuranosidase, galactase, and amylase;

<23> The method according to aspect <22>, wherein the protein is cellulase and/or xylanase; and <24> The method according to aspect <23>, wherein the filamentous fungus mutant strain is cultured in the presence of a cellulase inducer selected from the group consisting of cellulose, sophorose, and cellooligosaccharides (e.g., cellobiose, cellotriose, cellotetraose, cellopentaose, and cellohexaose), and cellulase or xylanase is collected from the culture product.

EXAMPLES

The present invention will now be described more specifically by Examples.

<Example 1> Production of Gene Disruption Strain (1) Construction of Plasmid DNA for Gene Disruption Using a plasmid pUC-tubB obtained by inserting a sequence from the upstream to the downstream (SEQ ID NO: 20) of the tubB gene (TRIREDRAFT_120830) derived from *Trichoderma reesei* into the HincII restriction endonuclease cutting site of pUC118 (Takara Bio Inc.) as a template and using forward primer 1 (SEQ ID NO: 15) and reverse primer 1 (SEQ ID NO: 16) shown in Table 1, PCR was carried out to amplify a fragment (A) of about 5.2 kbp. Separately, using acetamidase amdS (SEQ ID NO: 17) derived from *Aspergillus nidulans* as a template and using forward primer 2 (SEQ ID NO: 18) and reverse primer 2 (SEQ ID NO: 19) shown in Table 1, PCR was carried out to amplify a fragment (B) of about 3.1 kbp. The resulting DNA fragments (A) and (B) were treated in accordance with the protocol of In-Fusion HD Cloning Kit (Takara Bio Inc.) to construct a plasmid carrying amdS gene inserted into the tubB gene. This plasmid was transformed into *E. coli* DH5α competent Cells (Takara Bio Inc.), and a strain retaining the plasmid carrying the target gene was selected from the transformants obtained as ampicillin resistance strains by colony PCR. The selected transformant was cultured (at 37° C. for 1 day) using an ampicillin-containing LB medium, and the plasmid was then collected from the resulting cells and purified with High Pure Plasmid Isolation kit (Roche Diagnostics K.K.). Herein, the resulting vector is referred to as pUC-ΔtubB-amdS.

(2) Production of Transformant

*Trichoderma reesei* PC-3-7 strain (ATCC66589) and PCD-10 strain (FERM P-8172) were transformed with the vector constructed in the above (1). The introduction was performed by a protoplast PEG method (Biotechnol Bioeng. 2012, January 109(1): 92-99). The transformant was selected with a selection medium (2% glucose, 1.1 M sorbitol, 2% agar, 0.2% $KH_2PO_4$ (pH 5.5), 0.06% $CaCl_2.2H_2O$, 0.06% $CsCl_2$, 0.06% $MgSO_4.7H_2O$, 0.06% acetamide, 0.1% Trace element 1, wherein every "%" means w/v %) containing acetamide as a single nitrogen source. Trace element 1 has the following composition: 0.5 g $FeSO_4.7H_2O$, 0.2 g $CoCl_2$, 0.16 g $MnSO_4.7H_2O$, and 0.14 g $ZnSO_4.7H_2O$ were diluted with distilled water to 100 mL total. Among the resulting transformants, a transformant in which amdS had been inserted into the tubB gene site to cause gene disruption was selected by colony PCR. Transformants having gene disruption were named PC-3-7ΔtubB and PCD-10ΔtubB, respectively.

TABLE 1

| Primer | Sequence | SEQ ID NO |
|---|---|---|
| Forward primer 1 | CGTTTCCAGTGCGCAAAGTACCGCGCGCTTGACAA | 15 |
| Reverse primer 1 | CCAATGATGTGCGCATCTGGGAAATGTTCTTTGGC | 16 |
| Forward primer 2 | TGCGCACATCATTGGATAGG | 18 |
| Reverse primer 2 | TGCGCACTGGAAACGCAACC | 19 |

<Example 2> Study 1 on Culture of Transformant

The protein productivity of a transformant was evaluated as follows. For pre-culture, spores of *Trichoderma reesei* PC-3-7 and PCD-10, and PC-3-7ΔtubB, PCD-10ΔtubB produced in Example 1 were each inoculated at $1\times10^5$ cells/mL in 50 mL of a culture medium placed in a 500-mL flask and were shake-cultured at 28° C. and at 220 rpm (PRXYg-98R manufactured by Preci Co., Ltd.). The composition of the medium was as follows: 1% glucose, 0.14% $(NH_4)_2SO_4$, 0.2% $KH_2PO_4$, 0.03% $CaCl_2.2H_2O$, 0.03% $MgSO_4.7H_2O$, 0.1% Bacto Peptone (BD Difco), 0.05% Bacto Yeast extract (BD Difco), 0.1% Tween 80, 0.1% Trace element 2, and 50 mM tartaric acid buffer (pH 4.0). The composition of Trace element 2 was as follows: 6 mg $H_3BO_3$, 26 mg $(NH_4)_6Mo_7O_{24}.4H_2O$, 100 mg $FeCl_3.6H_2O$, 40 mg $CuSO_4.5H_2O$, 8 mg $MnCl_2.4H_2O$, and 200 mg $ZnCl_2$ were diluted with distilled water to 100 mL total.

After the pre-culture for 2 days, main culture was performed using BTR-25NA1S-8M (manufactured by Biott Corporation) as a jar fermentor. Ten percent (v/v %) of the pre-culture broth was inoculated and was cultured for 5 days. Crystalline cellulose, Avicel PH-101 (Sigma-Aldrich), was used as a carbon source at a concentration of 10%, and other culture medium components used were as follows: 0.42% $(NH_4)_2SO_4$, 0.2% $KH_2PO_4$, 0.03% $CaCl_2.2H_2O$, 0.03% $MgSO_4.7H_2O$, 0.1% Bacto Peptone, 0.05% Bacto Yeast extract, 0.1% Tween 80, 0.1% Trace element 2, and 0.2% Antifoam PE-L. The jar fermentor was set as follows: a temperature of 28° C., an air flow rate of 0.5 vvm, and a pH of 4.5 (adjusted with 5% ammonia water). The agitation rate was varied to maintain a constant DO of 3.0 ppm. The culture was performed for 5 days.

<Example 3> Study 2 on Culture of Transformant

The protein productivity of a transformant in the case of using another carbon source was evaluated as follows. In this investigation, PC-3-7 and PC-3-7ΔtubB were evaluated. The pre-culture was performed as in Example 2. The main culture was performed using BMZ-01KP2 (Biott Corporation) as the jar fermentor and using 10% Avicel PH-101+2.5% glucose or 10% Avicel PH-101+2% Xylan from Beechwood (Tokyo Chemical Industry Co., Ltd.) as the carbon source. Other conditions were the same as those in Example 2.

<Example 4> Measurement of Protein Concentration

The concentration of a protein was measured by a Bradford method. In the Bradford method, Quick Start Protein Assay (Bio-Rad Laboratories, Inc.) was used, and the protein concentration was calculated based on a standard curve drawn using bovine γ-globulin as a standard protein.

The results of measurement of protein concentration are shown in FIGS. 1 to 4. Since the transformant having tubB gene disruption showed protein productivity higher than that of the parent strain under every conditions, the effectiveness of tubB gene disruption on protein production was demonstrated.

---

The invention claimed is:

1. A method of producing a protein, the method comprising culturing a filamentous fungus mutant strain under conditions in which the protein is produced, wherein, in the mutant strain, a function of tubulin is reduced or lost, wherein the function of tubulin that is reduced or lost is (i) expression of α-tubulin or β-tubulin or both, and (ii) the formation of α-tubulin and β-tubulin heterodimers, as compared to that in the mutant's parent strain, and
collecting the protein from a culture product of the culturing.

2. The method according to claim 1, wherein the expression of α-tubulin is reduced or lost.

3. The method according to claim 1, wherein the expression of β-tubulin is reduced or lost.

4. The method according to claim 1, wherein the reduced or lost function of tubulin is the result of deleting or inactivating a gene encoding α-tubulin.

5. The method according to claim 1, wherein the reduced or lost function of tubulin is the result of deleting or inactivating a gene encoding β-tubulin.

6. The method according to claim 4, wherein the gene encoding α-tubulin comprises any of the following polynucleotides (a) to (f):
(a) a polynucleotide having the nucleotide sequence of SEQ ID NO: 1 or 3;
(b) a polynucleotide having a nucleotide sequence with an identity of 80% or more with the nucleotide sequence of SEQ ID NO: 1 or 3 and encoding a protein that forms microtubules with β-tubulin in the mutant's parent strain;
(c) a polynucleotide that hybridizes to a complementary strand of the polynucleotide having the nucleotide sequence of SEQ ID NO: 1 or 3 under stringent conditions that require the polynucleotide that hybridizes to the complementary strand have 80% or more identity to SEQ ID NO: 1 or 3, and wherein the polynucleotide encodes a protein that forms microtubules with β-tubulin in the mutant's parent strain;
(d) a polynucleotide encoding a protein having the amino acid sequence of SEQ ID NO: 2 or 4;

(e) a polynucleotide encoding a protein having the amino acid sequence of SEQ ID NO: 2 or 4 in which one or several amino acids are deleted, substituted, added or inserted and that forms microtubules with β-tubulin in the mutant's parent strain; and (f) a polynucleotide encoding a protein having an amino acid sequence with an identity of 80% or more with the amino acid sequence of SEQ ID NO: 2 or 4 and that forms microtubules with β-tubulin in the mutant's parent strain.

7. The method according to claim 5, wherein the gene encoding β-tubulin is comprises any of the following polynucleotides (g) to (l):

(g) a polynucleotide having the nucleotide sequence of SEQ ID NO: 5, 7, 9, 11, or 13;

(h) a polynucleotide having a nucleotide sequence with an identity of 80% or more with the nucleotide sequence of SEQ ID NO: 5, 7, 9, 11, or 13 and encoding a protein that forms microtubules with α-tubulin in the mutant's parent strain;

(i) a polynucleotide that hybridizes to a complementary strand of the polynucleotide having the nucleotide sequence of SEQ ID NO: 5, 7, 9, 11, or 13 under stringent conditions that require the polynucleotide that hybridizes to the complementary strand have 80% or more identity to SEQ ID NO: 5, 7, 9, 11 or 13, and wherein the polynucleotide encodes a protein that forms microtubules with α-tubulin in the mutant's parent strain;

(j) a polynucleotide encoding a protein having the amino acid sequence of SEQ ID NO: 6, 8, 10, 12, or 14;

(k) a polynucleotide encoding a protein having the amino acid sequence of SEQ ID NO: 6, 8, 10, 12, or 14 in which one or several amino acids are deleted, substituted, added or inserted and that forms microtubules with α-tubulin in the mutant's parent strain; and (l) a polynucleotide encoding a protein having an amino acid sequence with an identity of 80% or more with the amino acid sequence of SEQ ID NO: 6, 8, 10, 12, or 14 and that forms microtubules with α-tubulin in the mutant's parent strain.

8. The method according to claim 1, wherein the filamentous fungus is a filamentous fungus belonging to *Acremonium*, *Aspergillus*, *Chrysosporium*, *Fusarium*, *Humicola*, *Myceliophthora*, *Neurospora*, *Penicillium*, *Talaromyces*, *Thermoascus*, *Thielavia*, or *Trichoderma*.

9. The method according to claim 8, wherein the filamentous fungus is a *Trichoderma* filamentous fungus.

10. The method according to claim 1, wherein the protein is one or more selected from the group consisting of cellulase, xylanase, protease, lipase, exoglucanase, endoglucanase, β-glucosidase, mannase, arabinase, arabinofuranosidase, galactase, and amylase.

11. The method according to claim 10, wherein the protein is cellulase and/or xylanase.

12. The method according to claim 11, wherein the filamentous fungus mutant strain is cultured in the presence of a cellulase inducer selected from the group consisting of cellulose, sophorose, and a cellooligosaccharide, and cellulase or xylanase is collected from a culture product.

13. The method of claim 4, wherein the protein encoded by the α-tubulin gene has the amino acid sequence of SEQ ID NO:2.

14. The method of claim 5, wherein the protein encoded by the β-tubulin gene has the amino acid sequence of SEQ ID NO: 6.

* * * * *

SEQUENCE LISTING

```
<160> NUMBER OF SEQ ID NOS: 20

<210> SEQ ID NO 1
<211> LENGTH: 1359
<212> TYPE: DNA
<213> ORGANISM: Trichoderma reesei
<220> FEATURE:
<221> NAME/KEY: CDS
<222> LOCATION: (1)..(1359)

<400> SEQUENCE: 1 atg aga ggc gag att ctg cat ctg cac gtc ggc cag gcc ggt gtt cag        48
Met Arg Gly Glu Ile Leu His Leu His Val Gly Gln Ala Gly Val Gln
1               5                   10                  15 ctc ggc aac gca gct tgg gag ctc tac tgt ctc gag cac ggc atc ggc        96
Leu Gly Asn Ala Ala Trp Glu Leu Tyr Cys Leu Glu His Gly Ile Gly
            20                  25                  30 cgc gac ggt cgc atc agc gcg gac gtc cag gac cgc gat gat ctg ggc       144
Arg Asp Gly Arg Ile Ser Ala Asp Val Gln Asp Arg Asp Asp Leu Gly
        35                  40                  45 tct ccc gac acc ttc ttc acc gag acc agc aac ggc aag cac gtg ccg       192
Ser Pro Asp Thr Phe Phe Thr Glu Thr Ser Asn Gly Lys His Val Pro
    50                  55                  60 cgg gcc atc ttc gtc gac ctc gac ccg tcc ccc atc gac gag atc cgg       240
Arg Ala Ile Phe Val Asp Leu Asp Pro Ser Pro Ile Asp Glu Ile Arg
65                  70                  75                  80 gcg ggc gac tac cgc cag ctg ttc cat ccg gaa ctg ctc atc agc ggc       288
Ala Gly Asp Tyr Arg Gln Leu Phe His Pro Glu Leu Leu Ile Ser Gly
                85                  90                  95 aag gag gat gcg gcc aac aac tat gcg cgc ggg cac tac acc gtc ggc       336
Lys Glu Asp Ala Ala Asn Asn Tyr Ala Arg Gly His Tyr Thr Val Gly
            100                 105                 110
```

```
aag gag atg att gac acc gtc atg gac aag atc cgc cgt gtc aca gac      384
Lys Glu Met Ile Asp Thr Val Met Asp Lys Ile Arg Arg Val Thr Asp
        115                 120                 125 aac tgt cac tcc ctc cag ggg ttt ctc atg ttc cac tcc ttt ggc ggc      432
Asn Cys His Ser Leu Gln Gly Phe Leu Met Phe His Ser Phe Gly Gly
    130                 135                 140 ggc act ggc tcc ggc ttt ggt gcg ctg atg ctt gag cgt ctg gcc acc      480
Gly Thr Gly Ser Gly Phe Gly Ala Leu Met Leu Glu Arg Leu Ala Thr
145                 150                 155                 160 gag tac ggc aag aag acg aag ctc gag ttt gcc gtc tac cca gct cct      528
Glu Tyr Gly Lys Lys Thr Lys Leu Glu Phe Ala Val Tyr Pro Ala Pro
                165                 170                 175 cgc acg tcc tcg gcc gtc gtc gag cct tac aat gca gtc ctc tcg acc      576
Arg Thr Ser Ser Ala Val Val Glu Pro Tyr Asn Ala Val Leu Ser Thr
            180                 185                 190 cac agc acc atc gag cac tcg gac tgc acc ttc ttg gtg gac aac gag      624
His Ser Thr Ile Glu His Ser Asp Cys Thr Phe Leu Val Asp Asn Glu
        195                 200                 205 gca gtc tat gac att tgc aag cgg aat ctc gac atc tct cgg ccg tcc      672
Ala Val Tyr Asp Ile Cys Lys Arg Asn Leu Asp Ile Ser Arg Pro Ser
    210                 215                 220 ttc gat cac ctc aac cgc ctc att gcc caa gtg gtc agc tcc atc acg      720
Phe Asp His Leu Asn Arg Leu Ile Ala Gln Val Val Ser Ser Ile Thr
225                 230                 235                 240 tcg tct ctg cga ttc gac ggc gcg ctc aac gtc gac ctg aac gag ttc      768
Ser Ser Leu Arg Phe Asp Gly Ala Leu Asn Val Asp Leu Asn Glu Phe
                245                 250                 255 cag acc aac ctg gtt cct ttc ccg cgc atc cac tac ccc ctg atc agc      816
Gln Thr Asn Leu Val Pro Phe Pro Arg Ile His Tyr Pro Leu Ile Ser
            260                 265                 270 tac gcc ccg gtt gtt tcc aca aag aag gcc tcc cac gaa agc ttc aag      864
Tyr Ala Pro Val Val Ser Thr Lys Lys Ala Ser His Glu Ser Phe Lys
        275                 280                 285 gtt cag gag ctg aca ctt cag tgc ttt gaa ccc aac aac cag atg gtc      912
Val Gln Glu Leu Thr Leu Gln Cys Phe Glu Pro Asn Asn Gln Met Val
    290                 295                 300 gtc tgc gac ccc cgc aac ggc aag tac atg gcc gtg gtc ctg ctg tat      960
Val Cys Asp Pro Arg Asn Gly Lys Tyr Met Ala Val Val Leu Leu Tyr
305                 310                 315                 320 cgc ggc gac gtc gtg act cgt gac tgc aca gtc gcc gtc gcc cac gtc     1008
Arg Gly Asp Val Val Thr Arg Asp Cys Thr Val Ala Val Ala His Val
                325                 330                 335 aag gcc aag gca acc ttc aac atg gtc gac tgg tgc ccc acg ggc ttc     1056
Lys Ala Lys Ala Thr Phe Asn Met Val Asp Trp Cys Pro Thr Gly Phe
            340                 345                 350 aag ctc ggc atc acc tac cag aag ccc acg gcc gtc ccc gtc gac gct     1104
Lys Leu Gly Ile Thr Tyr Gln Lys Pro Thr Ala Val Pro Val Asp Ala
        355                 360                 365 cag gag ggc ggc ctc gcc gcc gtc aag cgc tcc gtg tcc atg ctc tcc     1152
Gln Glu Gly Gly Leu Ala Ala Val Lys Arg Ser Val Ser Met Leu Ser
    370                 375                 380 aac acg acc gcc atc gcc gaa gcc tgg tcg cgg ctg gac tat aag ttt     1200
Asn Thr Thr Ala Ile Ala Glu Ala Trp Ser Arg Leu Asp Tyr Lys Phe
385                 390                 395                 400 gac ctc atg cac aac aag cgc gca ttt gtc cac tgg tac gtc ggc gag     1248
Asp Leu Met His Asn Lys Arg Ala Phe Val His Trp Tyr Val Gly Glu
                405                 410                 415 ggc atg gag gag ggc gag ttc tcg gag gcg cga gag gat ctg gct gct     1296
Gly Met Glu Glu Gly Glu Phe Ser Glu Ala Arg Glu Asp Leu Ala Ala
```

```
                    420             425             430
ctg gag agg gat tac gcg gag gtt gct gcc gac tct ttc gag cct gac    1344
Leu Glu Arg Asp Tyr Ala Glu Val Ala Ala Asp Ser Phe Glu Pro Asp
        435                 440                 445 gag act gcc gag tat                                                1359
Glu Thr Ala Glu Tyr
    450
```

<210> SEQ ID NO 2
<211> LENGTH: 453
<212> TYPE: PRT
<213> ORGANISM: Trichoderma reesei

<400> SEQUENCE: 2

```
Met Arg Gly Glu Ile Leu His Leu His Val Gly Gln Ala Gly Val Gln
1               5                   10                  15

Leu Gly Asn Ala Ala Trp Glu Leu Tyr Cys Leu Glu His Gly Ile Gly
            20                  25                  30

Arg Asp Gly Arg Ile Ser Ala Asp Val Gln Asp Arg Asp Asp Leu Gly
        35                  40                  45

Ser Pro Asp Thr Phe Phe Thr Glu Thr Ser Asn Gly Lys His Val Pro
    50                  55                  60

Arg Ala Ile Phe Val Asp Leu Asp Pro Ser Pro Ile Asp Glu Ile Arg
65                  70                  75                  80

Ala Gly Asp Tyr Arg Gln Leu Phe His Pro Glu Leu Leu Ile Ser Gly
                85                  90                  95

Lys Glu Asp Ala Ala Asn Asn Tyr Ala Arg Gly His Tyr Thr Val Gly
            100                 105                 110

Lys Glu Met Ile Asp Thr Val Met Asp Lys Ile Arg Arg Val Thr Asp
        115                 120                 125

Asn Cys His Ser Leu Gln Gly Phe Leu Met Phe His Ser Phe Gly Gly
    130                 135                 140

Gly Thr Gly Ser Gly Phe Gly Ala Leu Met Leu Glu Arg Leu Ala Thr
145                 150                 155                 160

Glu Tyr Gly Lys Lys Thr Lys Leu Glu Phe Ala Val Tyr Pro Ala Pro
                165                 170                 175

Arg Thr Ser Ser Ala Val Val Glu Pro Tyr Asn Ala Val Leu Ser Thr
            180                 185                 190

His Ser Thr Ile Glu His Ser Asp Cys Thr Phe Leu Val Asp Asn Glu
        195                 200                 205

Ala Val Tyr Asp Ile Cys Lys Arg Asn Leu Asp Ile Ser Arg Pro Ser
    210                 215                 220

Phe Asp His Leu Asn Arg Leu Ile Ala Gln Val Val Ser Ser Ile Thr
225                 230                 235                 240

Ser Ser Leu Arg Phe Asp Gly Ala Leu Asn Val Asp Leu Asn Glu Phe
                245                 250                 255

Gln Thr Asn Leu Val Pro Phe Pro Arg Ile His Tyr Pro Leu Ile Ser
            260                 265                 270

Tyr Ala Pro Val Val Ser Thr Lys Lys Ala Ser His Glu Ser Phe Lys
        275                 280                 285

Val Gln Glu Leu Thr Leu Gln Cys Phe Glu Pro Asn Asn Gln Met Val
    290                 295                 300

Val Cys Asp Pro Arg Asn Gly Lys Tyr Met Ala Val Val Leu Leu Tyr
305                 310                 315                 320

Arg Gly Asp Val Val Thr Arg Asp Cys Thr Val Ala Val Ala His Val
```

```
                        325                 330                 335
Lys Ala Lys Ala Thr Phe Asn Met Val Asp Trp Cys Pro Thr Gly Phe
            340                 345                 350
Lys Leu Gly Ile Thr Tyr Gln Lys Pro Thr Ala Val Pro Val Asp Ala
        355                 360                 365
Gln Glu Gly Gly Leu Ala Ala Val Lys Arg Ser Val Ser Met Leu Ser
    370                 375                 380
Asn Thr Thr Ala Ile Ala Glu Ala Trp Ser Arg Leu Asp Tyr Lys Phe
385                 390                 395                 400
Asp Leu Met His Asn Lys Arg Ala Phe Val His Trp Tyr Val Gly Glu
                405                 410                 415
Gly Met Glu Glu Gly Glu Phe Ser Glu Ala Arg Glu Asp Leu Ala Ala
            420                 425                 430
Leu Glu Arg Asp Tyr Ala Glu Val Ala Ala Asp Ser Phe Glu Pro Asp
        435                 440                 445
Glu Thr Ala Glu Tyr
    450

<210> SEQ ID NO 3
<211> LENGTH: 1347
<212> TYPE: DNA
<213> ORGANISM: Trichoderma reesei
<220> FEATURE:
<221> NAME/KEY: CDS
<222> LOCATION: (1)..(1347)

<400> SEQUENCE: 3 atg cgt gag gtt atc agc atc aac gtc ggc cag gct ggt tgc cag att        48
Met Arg Glu Val Ile Ser Ile Asn Val Gly Gln Ala Gly Cys Gln Ile
1               5                   10                  15 gcc aac tcc tgc tgg gag ctc tac tgc ctt gag cac ggt atc cag ccc        96
Ala Asn Ser Cys Trp Glu Leu Tyr Cys Leu Glu His Gly Ile Gln Pro
            20                  25                  30 gat ggt tac ctc act gag gag cgc aag gct cag gac ccc gac cag ggt       144
Asp Gly Tyr Leu Thr Glu Glu Arg Lys Ala Gln Asp Pro Asp Gln Gly
        35                  40                  45 ttc agc acc ttc ttc tcc gag act ggc cag ggc aag tat gtc ccc cgc       192
Phe Ser Thr Phe Phe Ser Glu Thr Gly Gln Gly Lys Tyr Val Pro Arg
    50                  55                  60 gcc atc tac tgc gac ttg gag ccc aat gtc gtc gac gag gtc cga acc       240
Ala Ile Tyr Cys Asp Leu Glu Pro Asn Val Val Asp Glu Val Arg Thr
65                  70                  75                  80 ggt cct tac cgc aac ctt ttc cac ccg gag atg atg atc acc ggc aag       288
Gly Pro Tyr Arg Asn Leu Phe His Pro Glu Met Met Ile Thr Gly Lys
                85                  90                  95 gag gat gcc tcc aac aac tac gct cgt ggc cac tac acc gtc ggc aag       336
Glu Asp Ala Ser Asn Asn Tyr Ala Arg Gly His Tyr Thr Val Gly Lys
            100                 105                 110 gag ctg att gag ggc gtg ctc gac aag atc cgc cgt gtc gcc gac aac       384
Glu Leu Ile Glu Gly Val Leu Asp Lys Ile Arg Arg Val Ala Asp Asn
        115                 120                 125 tgc gtc ggt ctc cag ggc ttc ctc gtc ttc cac tcc ttc ggt ggt ggt       432
Cys Val Gly Leu Gln Gly Phe Leu Val Phe His Ser Phe Gly Gly Gly
    130                 135                 140 acc ggt tct ggt ttc gga gcc ctc ctg atg gag cgc ctg tct gtc gac       480
Thr Gly Ser Gly Phe Gly Ala Leu Leu Met Glu Arg Leu Ser Val Asp
145                 150                 155                 160 tac ggc aag aag agc aag ctc gag ttc tgc gtc tac cct gct cct cag       528
Tyr Gly Lys Lys Ser Lys Leu Glu Phe Cys Val Tyr Pro Ala Pro Gln
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 165 |     |     |     |     | 170 |     |     |     |     | 175 |     |      |
| acc | gcc | acc | tcc | gtc | gtt | gag | ccc | tac | aac | tcc | atc | ctc | acc | acc | cac | 576  |
| Thr | Ala | Thr | Ser | Val | Val | Glu | Pro | Tyr | Asn | Ser | Ile | Leu | Thr | Thr | His |      |
|     |     |     | 180 |     |     |     |     | 185 |     |     |     |     | 190 |     |     |      |
| acc | acc | ctg | gag | cac | tcc | gac | tgc | tcc | ttc | atg | gtc | gac | aac | gag | gcc | 624  |
| Thr | Thr | Leu | Glu | His | Ser | Asp | Cys | Ser | Phe | Met | Val | Asp | Asn | Glu | Ala |      |
|     |     | 195 |     |     |     |     | 200 |     |     |     |     | 205 |     |     |     |      |
| atc | tac | gac | atc | tgc | cgt | cgc | aac | ctc | ggc | ctc | gag | cgc | ccc | aac | tac | 672  |
| Ile | Tyr | Asp | Ile | Cys | Arg | Arg | Asn | Leu | Gly | Leu | Glu | Arg | Pro | Asn | Tyr |      |
| 210 |     |     |     |     | 215 |     |     |     |     | 220 |     |     |     |     |     |      |
| gag | aac | ctc | aac | cgc | ctg | att | gct | cag | gtc | gtt | tct | tcc | atc | acc | gct | 720  |
| Glu | Asn | Leu | Asn | Arg | Leu | Ile | Ala | Gln | Val | Val | Ser | Ser | Ile | Thr | Ala |      |
| 225 |     |     |     | 230 |     |     |     |     | 235 |     |     |     |     | 240 |     |      |
| tcc | ctg | cgt | ttc | gat | ggc | tcc | ctc | aac | gtt | gat | ctg | aac | gaa | ttc | cag | 768  |
| Ser | Leu | Arg | Phe | Asp | Gly | Ser | Leu | Asn | Val | Asp | Leu | Asn | Glu | Phe | Gln |      |
|     |     |     |     | 245 |     |     |     |     | 250 |     |     |     |     | 255 |     |      |
| acc | aac | ctg | gtg | ccc | tac | cct | cgt | atc | cac | ttc | cct | ctg | gtc | gcc | tac | 816  |
| Thr | Asn | Leu | Val | Pro | Tyr | Pro | Arg | Ile | His | Phe | Pro | Leu | Val | Ala | Tyr |      |
|     |     |     | 260 |     |     |     |     | 265 |     |     |     |     | 270 |     |     |      |
| gcc | ccc | gtc | atc | tcg | gcc | gcc | aag | gct | gcc | cac | gag | gcc | aac | tcc | gtc | 864  |
| Ala | Pro | Val | Ile | Ser | Ala | Ala | Lys | Ala | Ala | His | Glu | Ala | Asn | Ser | Val |      |
|     |     | 275 |     |     |     |     | 280 |     |     |     |     | 285 |     |     |     |      |
| cag | gag | atg | acc | atg | tcc | tgc | ttc | gag | ccc | aac | aac | cag | atg | gtc | aag | 912  |
| Gln | Glu | Met | Thr | Met | Ser | Cys | Phe | Glu | Pro | Asn | Asn | Gln | Met | Val | Lys |      |
|     | 290 |     |     |     |     | 295 |     |     |     |     | 300 |     |     |     |     |      |
| tgt | gac | ccc | cgc | aac | ggc | aag | tac | atg | gcc | acc | tgc | ctg | ctg | tac | cgc | 960  |
| Cys | Asp | Pro | Arg | Asn | Gly | Lys | Tyr | Met | Ala | Thr | Cys | Leu | Leu | Tyr | Arg |      |
| 305 |     |     |     |     | 310 |     |     |     |     | 315 |     |     |     |     | 320 |      |
| ggt | gac | gtc | gtc | ccc | aac | gac | gcc | cac | aac | gcc | gtc | gcc | acc | ctc | aag | 1008 |
| Gly | Asp | Val | Val | Pro | Asn | Asp | Ala | His | Asn | Ala | Val | Ala | Thr | Leu | Lys |      |
|     |     |     |     | 325 |     |     |     |     | 330 |     |     |     |     | 335 |     |      |
| acc | aag | cgc | acc | atc | cag | ttc | gtc | gac | tgg | tgc | cct | acc | ggt | ttc | aag | 1056 |
| Thr | Lys | Arg | Thr | Ile | Gln | Phe | Val | Asp | Trp | Cys | Pro | Thr | Gly | Phe | Lys |      |
|     |     |     | 340 |     |     |     |     | 345 |     |     |     |     | 350 |     |     |      |
| ctg | ggt | atc | tgc | tac | cag | gct | ccc | gag | aac | gtg | ccc | aac | ggc | gac | ctc | 1104 |
| Leu | Gly | Ile | Cys | Tyr | Gln | Ala | Pro | Glu | Asn | Val | Pro | Asn | Gly | Asp | Leu |      |
|     |     | 355 |     |     |     |     | 360 |     |     |     |     | 365 |     |     |     |      |
| gcc | aag | gtc | aac | cgc | gct | gtc | tgc | atg | ctg | tcc | aac | acc | acc | gcc | atc | 1152 |
| Ala | Lys | Val | Asn | Arg | Ala | Val | Cys | Met | Leu | Ser | Asn | Thr | Thr | Ala | Ile |      |
|     | 370 |     |     |     |     | 375 |     |     |     |     | 380 |     |     |     |     |      |
| gcc | gag | gcc | tgg | tcc | tcc | ctc | tcc | ctc | aag | ttc | gac | ctc | atg | cac | tcc | 1200 |
| Ala | Glu | Ala | Trp | Ser | Ser | Leu | Ser | Leu | Lys | Phe | Asp | Leu | Met | His | Ser |      |
| 385 |     |     |     |     | 390 |     |     |     |     | 395 |     |     |     |     | 400 |      |
| aag | cgt | gcc | ttc | gtc | cac | tgg | tac | gtc | ggt | gag | ggt | atg | gag | gag | ggt | 1248 |
| Lys | Arg | Ala | Phe | Val | His | Trp | Tyr | Val | Gly | Glu | Gly | Met | Glu | Glu | Gly |      |
|     |     |     |     | 405 |     |     |     |     | 410 |     |     |     |     | 415 |     |      |
| gaa | ttc | tcc | gag | gcc | cgt | gag | gat | ctc | gct | gcc | ctg | gag | cgc | gat | tac | 1296 |
| Glu | Phe | Ser | Glu | Ala | Arg | Glu | Asp | Leu | Ala | Ala | Leu | Glu | Arg | Asp | Tyr |      |
|     |     |     | 420 |     |     |     |     | 425 |     |     |     |     | 430 |     |     |      |
| gag | gag | gtt | gcc | gcc | gac | tct | ctc | gac | aac | gag | gag | atg | gag | gct | gag | 1344 |
| Glu | Glu | Val | Ala | Ala | Asp | Ser | Leu | Asp | Asn | Glu | Glu | Met | Glu | Ala | Glu |      |
|     |     | 435 |     |     |     |     | 440 |     |     |     |     | 445 |     |     |     |      |
| tac |     |     |     |     |     |     |     |     |     |     |     |     |     |     |     | 1347 |
| Tyr |     |     |     |     |     |     |     |     |     |     |     |     |     |     |     |      |

<210> SEQ ID NO 4
<211> LENGTH: 449
<212> TYPE: PRT
<213> ORGANISM: Trichoderma reesei -continued

<400> SEQUENCE: 4

```
Met Arg Glu Val Ile Ser Ile Asn Val Gly Gln Ala Gly Cys Gln Ile
1               5                   10                  15

Ala Asn Ser Cys Trp Glu Leu Tyr Cys Leu Glu His Gly Ile Gln Pro
            20                  25                  30

Asp Gly Tyr Leu Thr Glu Arg Lys Ala Gln Asp Pro Asp Gln Gly
        35                  40                  45

Phe Ser Thr Phe Phe Ser Glu Thr Gly Gln Gly Lys Tyr Val Pro Arg
    50                  55                  60

Ala Ile Tyr Cys Asp Leu Glu Pro Asn Val Val Asp Glu Val Arg Thr
65                  70                  75                  80

Gly Pro Tyr Arg Asn Leu Phe His Pro Glu Met Met Ile Thr Gly Lys
                85                  90                  95

Glu Asp Ala Ser Asn Asn Tyr Ala Arg Gly His Tyr Thr Val Gly Lys
            100                 105                 110

Glu Leu Ile Glu Gly Val Leu Asp Lys Ile Arg Arg Val Ala Asp Asn
        115                 120                 125

Cys Val Gly Leu Gln Gly Phe Leu Val Phe His Ser Phe Gly Gly Gly
130                 135                 140

Thr Gly Ser Gly Phe Gly Ala Leu Leu Met Glu Arg Leu Ser Val Asp
145                 150                 155                 160

Tyr Gly Lys Lys Ser Lys Leu Glu Phe Cys Val Tyr Pro Ala Pro Gln
                165                 170                 175

Thr Ala Thr Ser Val Val Glu Pro Tyr Asn Ser Ile Leu Thr Thr His
            180                 185                 190

Thr Thr Leu Glu His Ser Asp Cys Ser Phe Met Val Asp Asn Glu Ala
        195                 200                 205

Ile Tyr Asp Ile Cys Arg Arg Asn Leu Gly Leu Glu Arg Pro Asn Tyr
210                 215                 220

Glu Asn Leu Asn Arg Leu Ile Ala Gln Val Val Ser Ser Ile Thr Ala
225                 230                 235                 240

Ser Leu Arg Phe Asp Gly Ser Leu Asn Val Asp Leu Asn Glu Phe Gln
                245                 250                 255

Thr Asn Leu Val Pro Tyr Pro Arg Ile His Phe Pro Leu Val Ala Tyr
            260                 265                 270

Ala Pro Val Ile Ser Ala Ala Lys Ala Ala His Glu Ala Asn Ser Val
        275                 280                 285

Gln Glu Met Thr Met Ser Cys Phe Glu Pro Asn Asn Gln Met Val Lys
290                 295                 300

Cys Asp Pro Arg Asn Gly Lys Tyr Met Ala Thr Cys Leu Leu Tyr Arg
305                 310                 315                 320

Gly Asp Val Val Pro Asn Asp Ala His Asn Ala Val Ala Thr Leu Lys
                325                 330                 335

Thr Lys Arg Thr Ile Gln Phe Val Asp Trp Cys Pro Thr Gly Phe Lys
            340                 345                 350

Leu Gly Ile Cys Tyr Gln Ala Pro Glu Asn Val Pro Asn Gly Asp Leu
        355                 360                 365

Ala Lys Val Asn Arg Ala Val Cys Met Leu Ser Asn Thr Thr Ala Ile
370                 375                 380

Ala Glu Ala Trp Ser Ser Leu Ser Leu Lys Phe Asp Leu Met His Ser
385                 390                 395                 400

Lys Arg Ala Phe Val His Trp Tyr Val Gly Glu Gly Met Glu Glu Gly
                405                 410                 415
```

```
Glu Phe Ser Glu Ala Arg Glu Asp Leu Ala Ala Leu Glu Arg Asp Tyr
            420                 425                 430

Glu Glu Val Ala Ala Asp Ser Leu Asp Asn Glu Met Glu Ala Glu
        435                 440                 445

Tyr

<210> SEQ ID NO 5
<211> LENGTH: 1335
<212> TYPE: DNA
<213> ORGANISM: Trichoderma reesei
<220> FEATURE:
<221> NAME/KEY: CDS
<222> LOCATION: (1)..(1335)

<400> SEQUENCE: 5 atg cgt gag att gtt cac ctc cag acc ggt cag tgt ggt aac caa gtt    48
Met Arg Glu Ile Val His Leu Gln Thr Gly Gln Cys Gly Asn Gln Val
1               5                   10                  15 ggt tct gcc ttc tgg cag acc atc tct ggc gag cac ggc ctc gac gcc    96
Gly Ser Ala Phe Trp Gln Thr Ile Ser Gly Glu His Gly Leu Asp Ala
            20                  25                  30 agc ggt gtc tac ggt ggt acc tcg gac cag cag ctc gag cgt ctg aac   144
Ser Gly Val Tyr Gly Gly Thr Ser Asp Gln Gln Leu Glu Arg Leu Asn
        35                  40                  45 gtc tac ttc aac gag gct tct ggc aac aaa tat gtc ccc cgt gct gtc   192
Val Tyr Phe Asn Glu Ala Ser Gly Asn Lys Tyr Val Pro Arg Ala Val
    50                  55                  60 ctc gtc gac ctc gag ccc ggc acc atg gat gcc gtt cgc tcg ggc ccc   240
Leu Val Asp Leu Glu Pro Gly Thr Met Asp Ala Val Arg Ser Gly Pro
65                  70                  75                  80 ttt ggc cag ctg ttc cgc cct gac aac ttc gtc ttt ggc cag tct ggt   288
Phe Gly Gln Leu Phe Arg Pro Asp Asn Phe Val Phe Gly Gln Ser Gly
                85                  90                  95 gct ggt aac aat tgg gca aag ggt cac tac acc gag ggt gcc gag ctg   336
Ala Gly Asn Asn Trp Ala Lys Gly His Tyr Thr Glu Gly Ala Glu Leu
            100                 105                 110 gtt gac cag gtt ctc gat gtc gtt cgt cgc gag gcc gaa aac tgt gaa   384
Val Asp Gln Val Leu Asp Val Val Arg Arg Glu Ala Glu Asn Cys Glu
        115                 120                 125 tgc ctc cag ggt ttc cag att acg cac tcg ctg ggt ggt ggt acc ggt   432
Cys Leu Gln Gly Phe Gln Ile Thr His Ser Leu Gly Gly Gly Thr Gly
    130                 135                 140 tcc ggt atg ggt acc ctg ctg atc tcc aag atc cgt gag gag ttc ccc   480
Ser Gly Met Gly Thr Leu Leu Ile Ser Lys Ile Arg Glu Glu Phe Pro
145                 150                 155                 160 gat cgc atg atg gcc acg ttc tcc gtc gtc ccc tcg ccc aag gtc tcg   528
Asp Arg Met Met Ala Thr Phe Ser Val Val Pro Ser Pro Lys Val Ser
                165                 170                 175 gat acc gtt gtc gag ccc tac aac gcc acc ttg tct atg cac cag ctg   576
Asp Thr Val Val Glu Pro Tyr Asn Ala Thr Leu Ser Met His Gln Leu
            180                 185                 190 gtt gaa aat tcg gat gag acg ttc tgt atc gac aac gaa gcc ctg tac   624
Val Glu Asn Ser Asp Glu Thr Phe Cys Ile Asp Asn Glu Ala Leu Tyr
        195                 200                 205 gat atc tgc atg agg acg ctt aag ctg tcc aac ccc tca tac ggc gac   672
Asp Ile Cys Met Arg Thr Leu Lys Leu Ser Asn Pro Ser Tyr Gly Asp
    210                 215                 220 ctc aac cac ctg gtt tct gcc gtt atg tct ggt gtc tct acc tct ctc   720
Leu Asn His Leu Val Ser Ala Val Met Ser Gly Val Ser Thr Ser Leu
225                 230                 235                 240
```

```
cga ttc cct ggc cag ctc aac tcc gac ctt cgc aag ctc gct gtt aac      768
Arg Phe Pro Gly Gln Leu Asn Ser Asp Leu Arg Lys Leu Ala Val Asn
            245                 250                 255 atg gtg ccg ttc cct cgt ctg cac ttc ttc atg gtc ggc ttt gcg ccg      816
Met Val Pro Phe Pro Arg Leu His Phe Phe Met Val Gly Phe Ala Pro
            260                 265                 270 ctt acc agc cct gga gcg cac tcc ttc cgc gct gtt acc gtc ccc gag      864
Leu Thr Ser Pro Gly Ala His Ser Phe Arg Ala Val Thr Val Pro Glu
            275                 280                 285 ttg acc cag cag atg ctg gac ccc aag aac atg atg gcg gcc tct gat      912
Leu Thr Gln Gln Met Leu Asp Pro Lys Asn Met Met Ala Ala Ser Asp
            290                 295                 300 ttc cgc aac ggc cgc tac ctg acg tgc tcc acc atc ttc cgt ggc aag      960
Phe Arg Asn Gly Arg Tyr Leu Thr Cys Ser Thr Ile Phe Arg Gly Lys
305                 310                 315                 320 gtt gcc atg aag gag gtc gag gac cag atg cgc agc atc cag aac aag     1008
Val Ala Met Lys Glu Val Glu Asp Gln Met Arg Ser Ile Gln Asn Lys
                325                 330                 335 aac tcg agc tac ttc gtc gag tgg att ccc aac aat atc cag acc gcg     1056
Asn Ser Ser Tyr Phe Val Glu Trp Ile Pro Asn Asn Ile Gln Thr Ala
            340                 345                 350 ctc tgc tct atc ccc ccc aag ggt ctc aag atc tct tcc acc ttt gtc     1104
Leu Cys Ser Ile Pro Pro Lys Gly Leu Lys Ile Ser Ser Thr Phe Val
            355                 360                 365 ggt aac tct acc gcc atc cag gag atc ttc cgc cgc gtt ggt gaa cag     1152
Gly Asn Ser Thr Ala Ile Gln Glu Ile Phe Arg Arg Val Gly Glu Gln
            370                 375                 380 ttc acc gcc atg ttc cgg cgt aag gct ttc ttg cac tgg tat act agc     1200
Phe Thr Ala Met Phe Arg Arg Lys Ala Phe Leu His Trp Tyr Thr Ser
385                 390                 395                 400 gag ggt atg gac gag atg gag ttc acg gag gcc gag tcc aac atg aac     1248
Glu Gly Met Asp Glu Met Glu Phe Thr Glu Ala Glu Ser Asn Met Asn
                405                 410                 415 gat ctc gtc tcc gag tac cag caa tac cag gat gct acg gct gat gat     1296
Asp Leu Val Ser Glu Tyr Gln Gln Tyr Gln Asp Ala Thr Ala Asp Asp
            420                 425                 430 ggc gag gag tat gag gag gag atg ccc att gac gag cag                 1335
Gly Glu Glu Tyr Glu Glu Glu Met Pro Ile Asp Glu Gln
            435                 440                 445

<210> SEQ ID NO 6
<211> LENGTH: 445
<212> TYPE: PRT
<213> ORGANISM: Trichoderma reesei

<400> SEQUENCE: 6

Met Arg Glu Ile Val His Leu Gln Thr Gly Gln Cys Gly Asn Gln Val
1               5                   10                  15

Gly Ser Ala Phe Trp Gln Thr Ile Ser Gly Glu His Gly Leu Asp Ala
            20                  25                  30

Ser Gly Val Tyr Gly Gly Thr Ser Asp Gln Gln Leu Glu Arg Leu Asn
        35                  40                  45

Val Tyr Phe Asn Glu Ala Ser Gly Asn Lys Tyr Val Pro Arg Ala Val
    50                  55                  60

Leu Val Asp Leu Glu Pro Gly Thr Met Asp Ala Val Arg Ser Gly Pro
65                  70                  75                  80

Phe Gly Gln Leu Phe Arg Pro Asp Asn Phe Val Phe Gly Gln Ser Gly
                85                  90                  95
```

Ala Gly Asn Asn Trp Ala Lys Gly His Tyr Thr Glu Gly Ala Glu Leu
            100                 105                 110

Val Asp Gln Val Leu Asp Val Val Arg Arg Glu Ala Glu Asn Cys Glu
        115                 120                 125

Cys Leu Gln Gly Phe Gln Ile Thr His Ser Leu Gly Gly Gly Thr Gly
    130                 135                 140

Ser Gly Met Gly Thr Leu Leu Ile Ser Lys Ile Arg Glu Glu Phe Pro
145                 150                 155                 160

Asp Arg Met Met Ala Thr Phe Ser Val Val Pro Ser Pro Lys Val Ser
                165                 170                 175

Asp Thr Val Val Glu Pro Tyr Asn Ala Thr Leu Ser Met His Gln Leu
            180                 185                 190

Val Glu Asn Ser Asp Glu Thr Phe Cys Ile Asp Asn Glu Ala Leu Tyr
        195                 200                 205

Asp Ile Cys Met Arg Thr Leu Lys Leu Ser Asn Pro Ser Tyr Gly Asp
    210                 215                 220

Leu Asn His Leu Val Ser Ala Val Met Ser Gly Val Ser Thr Ser Leu
225                 230                 235                 240

Arg Phe Pro Gly Gln Leu Asn Ser Asp Leu Arg Lys Leu Ala Val Asn
                245                 250                 255

Met Val Pro Phe Pro Arg Leu His Phe Phe Met Val Gly Phe Ala Pro
            260                 265                 270

Leu Thr Ser Pro Gly Ala His Ser Phe Arg Ala Val Thr Val Pro Glu
        275                 280                 285

Leu Thr Gln Gln Met Leu Asp Pro Lys Asn Met Met Ala Ala Ser Asp
    290                 295                 300

Phe Arg Asn Gly Arg Tyr Leu Thr Cys Ser Thr Ile Phe Arg Gly Lys
305                 310                 315                 320

Val Ala Met Lys Glu Val Glu Asp Gln Met Arg Ser Ile Gln Asn Lys
                325                 330                 335

Asn Ser Ser Tyr Phe Val Glu Trp Ile Pro Asn Asn Ile Gln Thr Ala
            340                 345                 350

Leu Cys Ser Ile Pro Pro Lys Gly Leu Lys Ile Ser Ser Thr Phe Val
        355                 360                 365

Gly Asn Ser Thr Ala Ile Gln Glu Ile Phe Arg Val Gly Glu Gln
    370                 375                 380

Phe Thr Ala Met Phe Arg Arg Lys Ala Phe Leu His Trp Tyr Thr Ser
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Asp Asp
            420                 425                 430

Gly Glu Glu Tyr Glu Glu Glu Met Pro Ile Asp Glu Gln
        435                 440                 445

<210> SEQ ID NO 7
<211> LENGTH: 1338
<212> TYPE: DNA
<213> ORGANISM: Trichoderma reesei
<220> FEATURE:
<221> NAME/KEY: CDS
<222> LOCATION: (1)..(1338)

<400> SEQUENCE: 7 atg cgt gag att gtt cac atc cag acc ggc cag tgc ggt aac caa atc      48
Met Arg Glu Ile Val His Ile Gln Thr Gly Gln Cys Gly Asn Gln Ile -continued

| | | | | | | | | | | | | | | | | |
|---|---|---|---|---|---|---|---|---|---|---|---|---|---|---|---|---|
| 1 | | | | 5 | | | | | 10 | | | | | 15 | | |

```
ggt gcc gcc ttt tgg cag acc atc tct ggc gag cac ggc ctc gac agc      96
Gly Ala Ala Phe Trp Gln Thr Ile Ser Gly Glu His Gly Leu Asp Ser
         20                  25                  30 aat ggt atc tat gga ggt tct tcc gag ctc cag ctg gag cgc atg aac     144
Asn Gly Ile Tyr Gly Gly Ser Ser Glu Leu Gln Leu Glu Arg Met Asn
     35                  40                  45 gtc tac ttc aac gag gcc aac aac aag tat gtt cct cgc gct gtc         192
Val Tyr Phe Asn Glu Ala Asn Asn Lys Tyr Val Pro Arg Ala Val
 50                  55                  60 ctc gtc gat ctc gag ccc ggt acc atg gac gcc gtc cgt gcc ggt ccc     240
Leu Val Asp Leu Glu Pro Gly Thr Met Asp Ala Val Arg Ala Gly Pro
65                  70                  75                  80 ttc ggt cag ctc ttc cga ccc gac aac ttc atc ttc ggc cag tcc agt     288
Phe Gly Gln Leu Phe Arg Pro Asp Asn Phe Ile Phe Gly Gln Ser Ser
                 85                  90                  95 gcc ggc aac aac tgg gcc aag ggc cac tac acc gag ggc gct gag ctc     336
Ala Gly Asn Asn Trp Ala Lys Gly His Tyr Thr Glu Gly Ala Glu Leu
             100                 105                 110 gtc gac aac gtc ctc gac gtg atc cgc cgt gag gcc gag ggc tgc gac     384
Val Asp Asn Val Leu Asp Val Ile Arg Arg Glu Ala Glu Gly Cys Asp
             115                 120                 125 tgc ctg cag ggc ttc cag atc acc cac tcc ctc ggc ggt ggt acc gga     432
Cys Leu Gln Gly Phe Gln Ile Thr His Ser Leu Gly Gly Gly Thr Gly
    130                 135                 140 tcc ggc atg ggc acg ctt ctc atc tcc aag atc cgc gag gaa ttc ccc     480
Ser Gly Met Gly Thr Leu Leu Ile Ser Lys Ile Arg Glu Glu Phe Pro
145                 150                 155                 160 gac cga atg atg gcc acc ttc tcc gtc atg ccg tcc ccc aag gtg tcc     528
Asp Arg Met Met Ala Thr Phe Ser Val Met Pro Ser Pro Lys Val Ser
                 165                 170                 175 gac acc gtc gtt gaa ccc tac aac gcc acc ctc tcc gtc cac cag ctg     576
Asp Thr Val Val Glu Pro Tyr Asn Ala Thr Leu Ser Val His Gln Leu
             180                 185                 190 gtc gag aac tcg gac gag acc ttc tgc att gac aac gag gct ctc tac     624
Val Glu Asn Ser Asp Glu Thr Phe Cys Ile Asp Asn Glu Ala Leu Tyr
             195                 200                 205 gac atc tgc atg cgc acc ctg aag ctg tct aac cct gcc tac ggt gac     672
Asp Ile Cys Met Arg Thr Leu Lys Leu Ser Asn Pro Ala Tyr Gly Asp
    210                 215                 220 ctg aac tac ctc gtc tcc gcc gtc atg tcg ggc att acc acg tgc ctg     720
Leu Asn Tyr Leu Val Ser Ala Val Met Ser Gly Ile Thr Thr Cys Leu
225                 230                 235                 240 cga ttc ccc ggt cag ctc aac tcg gac ctg cgc aag ctg gct gtc aac     768
Arg Phe Pro Gly Gln Leu Asn Ser Asp Leu Arg Lys Leu Ala Val Asn
                 245                 250                 255 atg gtt ccc ttc ccc cgt ctc cac ttc ttc atg gtc gga ttc gct ccc     816
Met Val Pro Phe Pro Arg Leu His Phe Phe Met Val Gly Phe Ala Pro
             260                 265                 270 ctg acg agc ccc ggc gcc cac tcc ttc cgt gcc gtc acc gtg ccg gaa     864
Leu Thr Ser Pro Gly Ala His Ser Phe Arg Ala Val Thr Val Pro Glu
             275                 280                 285 ctc acc cag caa atg ttc gac cct aag aac atg atg gct gct tct gac     912
Leu Thr Gln Gln Met Phe Asp Pro Lys Asn Met Met Ala Ala Ser Asp
    290                 295                 300 ttc cgc aac ggt cgc tac ctg acc tgc tgc tcc atc ttc cgt ggc aag     960
Phe Arg Asn Gly Arg Tyr Leu Thr Cys Cys Ser Ile Phe Arg Gly Lys
305                 310                 315                 320 gtt gcc atg aag gag gtt gag gac cag atg cga aac gtg cag aac aag    1008
```

-continued

```
                Val Ala Met Lys Glu Val Glu Asp Gln Met Arg Asn Val Gln Asn Lys
                                325                 330                 335 aac tcg acc tac ttc gtc gag tgg atc ccc aac aac atc cag act gcc      1056
Asn Ser Thr Tyr Phe Val Glu Trp Ile Pro Asn Asn Ile Gln Thr Ala
            340                 345                 350 ctt tgc gcc atc cct ccc cgt ggc ctg aag atg tcg tcc acc ttc atc      1104
Leu Cys Ala Ile Pro Pro Arg Gly Leu Lys Met Ser Ser Thr Phe Ile
            355                 360                 365 ggc aac tcc acg tcc atc cag gag ctg ttc aag cgt gtc ggc gag cag      1152
Gly Asn Ser Thr Ser Ile Gln Glu Leu Phe Lys Arg Val Gly Glu Gln
            370                 375                 380 ttc agc gcc atg ttc cgt cgc aag gcc ttc ttg cac tgg tac act ggc      1200
Phe Ser Ala Met Phe Arg Arg Lys Ala Phe Leu His Trp Tyr Thr Gly
385                 390                 395                 400 gag ggc atg gac gag atg gag ttc acc gag gcc gag tcc aac atg aac      1248
Glu Gly Met Asp Glu Met Glu Phe Thr Glu Ala Glu Ser Asn Met Asn
                405                 410                 415 gac ttg gtg tcg gaa tac cag cag tac cag gag gct ggt att gac gag      1296
Asp Leu Val Ser Glu Tyr Gln Gln Tyr Gln Glu Ala Gly Ile Asp Glu
            420                 425                 430 gag gag tac gag gag gag gag gcc ccc gcc gag cac gac gag              1338
Glu Glu Tyr Glu Glu Glu Glu Ala Pro Ala Glu His Asp Glu
            435                 440                 445

<210> SEQ ID NO 8
<211> LENGTH: 446
<212> TYPE: PRT
<213> ORGANISM: Trichoderma reesei

<400> SEQUENCE: 8

Met Arg Glu Ile Val His Ile Gln Thr Gly Gln Cys Gly Asn Gln Ile
1               5                   10                  15

Gly Ala Ala Phe Trp Gln Thr Ile Ser Gly Glu His Gly Leu Asp Ser
                20                  25                  30

Asn Gly Ile Tyr Gly Gly Ser Ser Glu Leu Gln Leu Glu Arg Met Asn
            35                  40                  45

Val Tyr Phe Asn Glu Ala Asn Asn Lys Tyr Val Pro Arg Ala Val
50                  55                  60

Leu Val Asp Leu Glu Pro Gly Thr Met Asp Ala Val Arg Ala Gly Pro
65                  70                  75                  80

Phe Gly Gln Leu Phe Arg Pro Asp Asn Phe Ile Phe Gly Gln Ser Ser
                85                  90                  95

Ala Gly Asn Asn Trp Ala Lys Gly His Tyr Thr Glu Gly Ala Glu Leu
            100                 105                 110

Val Asp Asn Val Leu Asp Val Ile Arg Arg Glu Ala Glu Gly Cys Asp
        115                 120                 125

Cys Leu Gln Gly Phe Gln Ile Thr His Ser Leu Gly Gly Gly Thr Gly
    130                 135                 140

Ser Gly Met Gly Thr Leu Leu Ile Ser Lys Ile Arg Glu Glu Phe Pro
145                 150                 155                 160

Asp Arg Met Met Ala Thr Phe Ser Val Met Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Ser Asp Glu Thr Phe Cys Ile Asp Asn Glu Ala Leu Tyr
        195                 200                 205

Asp Ile Cys Met Arg Thr Leu Lys Leu Ser Asn Pro Ala Tyr Gly Asp
```

```
                210                 215                 220
Leu Asn Tyr Leu Val Ser Ala Val Met Ser Gly Ile Thr Thr Cys Leu
225                 230                 235                 240

Arg Phe Pro Gly Gln Leu Asn Ser Asp Leu Arg Lys Leu Ala Val Asn
                245                 250                 255

Met Val Pro Phe Pro Arg Leu His Phe Met Val Gly Phe Ala Pro
                260                 265                 270

Leu Thr Ser Pro Gly Ala His Ser Phe Arg Ala Val Thr Val Pro Glu
                275                 280                 285

Leu Thr Gln Gln Met Phe Asp Pro Lys Asn Met Met Ala Ala Ser Asp
                290                 295                 300

Phe Arg Asn Gly Arg Tyr Leu Thr Cys Cys Ser Ile Phe Arg Gly Lys
305                 310                 315                 320

Val Ala Met Lys Glu Val Glu Asp Gln Met Arg Asn Val Gln Asn Lys
                325                 330                 335

Asn Ser Thr Tyr Phe Val Glu Trp Ile Pro Asn Asn Ile Gln Thr Ala
                340                 345                 350

Leu Cys Ala Ile Pro Pro Arg Gly Leu Lys Met Ser Ser Thr Phe Ile
                355                 360                 365

Gly Asn Ser Thr Ser Ile Gln Glu Leu Phe Lys Arg Val Gly Glu Gln
                370                 375                 380

Phe Ser Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Glu Ala Gly Ile Asp Glu
                420                 425                 430

Glu Glu Tyr Glu Glu Glu Ala Pro Ala Glu His Asp Glu
                435                 440                 445

<210> SEQ ID NO 9
<211> LENGTH: 1479
<212> TYPE: DNA
<213> ORGANISM: Trichoderma reesei
<220> FEATURE:
<221> NAME/KEY: CDS
<222> LOCATION: (1)..(1479)

<400> SEQUENCE: 9 atg cgc gaa ttg ata cag act cta aaa gag aac aag ata cca gtc ttt    48
Met Arg Glu Leu Ile Gln Thr Leu Lys Glu Asn Lys Ile Pro Val Phe
1               5                   10                  15 gcg cct gga gag ccg caa tac gag cga tca gtg gcc acg gtc aac ctc    96
Ala Pro Gly Glu Pro Gln Tyr Glu Arg Ser Val Ala Thr Val Asn Leu
                20                  25                  30 ttc tac cgg ttc gca aga ccc gac tgc gtt gtc cag cca cga aac gcg   144
Phe Tyr Arg Phe Ala Arg Pro Asp Cys Val Val Gln Pro Arg Asn Ala
                35                  40                  45 tct gac gtc caa gcc gtt gtc cga gag gcg aga aca aga cgc atc cac   192
Ser Asp Val Gln Ala Val Val Arg Glu Ala Arg Thr Arg Arg Ile His
        50                  55                  60 atc acg atc aag aat ggg ggc cat tca tac tcg ggc gcc tcc acc gcg   240
Ile Thr Ile Lys Asn Gly Gly His Ser Tyr Ser Gly Ala Ser Thr Ala
65                  70                  75                  80 gag aag gga atc tca cta gat ctg atg cag atg aac ggc gtc acg ctc   288
Glu Lys Gly Ile Ser Leu Asp Leu Met Gln Met Asn Gly Val Thr Leu
                85                  90                  95
```

-continued

| | | |
|---|---|---|
| aac atg aag act aag ctt gcc act gtc aaa ggc ggc gca caa tgg ggc<br>Asn Met Lys Thr Lys Leu Ala Thr Val Lys Gly Gly Ala Gln Trp Gly<br>100 105 110 | | 336 |
| cac gtt tac aag cag ttt gtg atc cgc aag att gac ggc tac gtt gtc<br>His Val Tyr Lys Gln Phe Val Ile Arg Lys Ile Asp Gly Tyr Val Val<br>115 120 125 | | 384 |
| aac ggt gga cgg tgt ccc acg gtg gga gtc agc ggc ttc acc ctc gga<br>Asn Gly Gly Arg Cys Pro Thr Val Gly Val Ser Gly Phe Thr Leu Gly<br>130 135 140 | | 432 |
| ggc ggc ctc agc ccg ttt acc agg agc ttc gga atg ggc tgt gac tcg<br>Gly Gly Leu Ser Pro Phe Thr Arg Ser Phe Gly Met Gly Cys Asp Ser<br>145 150 155 160 | | 480 |
| ctg gag gag gct acc ata gtc act gct agc gga gac aag gtc aag gtc<br>Leu Glu Glu Ala Thr Ile Val Thr Ala Ser Gly Asp Lys Val Lys Val<br>165 170 175 | | 528 |
| aag agg agc gat gac cct cga tcc gat aaa ggc agg ctc ttc tgg gcg<br>Lys Arg Ser Asp Asp Pro Arg Ser Asp Lys Gly Arg Leu Phe Trp Ala<br>180 185 190 | | 576 |
| ctc tgt ggc gcg ggg gga ggc aac ttt gga gtt gtc gtc gag atg aag<br>Leu Cys Gly Ala Gly Gly Gly Asn Phe Gly Val Val Val Glu Met Lys<br>195 200 205 | | 624 |
| ctg cgg atc gaa aag ctt caa ggc aac aaa gtc gtg gca ggc aga tac<br>Leu Arg Ile Glu Lys Leu Gln Gly Asn Lys Val Val Ala Gly Arg Tyr<br>210 215 220 | | 672 |
| acc tgg cac ccg gac ttt ggc ccg agc cat cat cca aga agg tcc gcg<br>Thr Trp His Pro Asp Phe Gly Pro Ser His His Pro Arg Arg Ser Ala<br>225 230 235 240 | | 720 |
| gac tac gcc gct acc atg acg cag ttt tat acg gca gat ttc cct aca<br>Asp Tyr Ala Ala Thr Met Thr Gln Phe Tyr Thr Ala Asp Phe Pro Thr<br>245 250 255 | | 768 |
| gag ctc acc att gac agc acg tgg ctg tgc gat ctt cag gag agc aga<br>Glu Leu Thr Ile Asp Ser Thr Trp Leu Cys Asp Leu Gln Glu Ser Arg<br>260 265 270 | | 816 |
| gat gcc atc agg ttc ctc gtc tac cac aac ggc ggc aaa gca gag ttc<br>Asp Ala Ile Arg Phe Leu Val Tyr His Asn Gly Gly Lys Ala Glu Phe<br>275 280 285 | | 864 |
| gac aag gtc att gac gac acc atc tcc tcc gtt cca ctg gcg acg cag<br>Asp Lys Val Ile Asp Asp Thr Ile Ser Ser Val Pro Leu Ala Thr Gln<br>290 295 300 | | 912 |
| ctc aaa agg cgc tct ctc gaa gag tca tct tgc cgc ttc ttg cat gag<br>Leu Lys Arg Arg Ser Leu Glu Glu Ser Ser Cys Arg Phe Leu His Glu<br>305 310 315 320 | | 960 |
| acg ctt gtt act caa tgg tca gag gag att gaa aag tca ctt cca ttg<br>Thr Leu Val Thr Gln Trp Ser Glu Glu Ile Glu Lys Ser Leu Pro Leu<br>325 330 335 | | 1008 |
| aac cta tct ttc aac aac tac gcc tcc ttt gtt ttc gaa aac gat cga<br>Asn Leu Ser Phe Asn Asn Tyr Ala Ser Phe Val Phe Glu Asn Asp Arg<br>340 345 350 | | 1056 |
| cga gat gta gtt gag aat atc tcg cgc atc atc cga cac aac atg gtc<br>Arg Asp Val Val Glu Asn Ile Ser Arg Ile Ile Arg His Asn Met Val<br>355 360 365 | | 1104 |
| agg ttt cga gaa aag ttc acc ggg gat cgc ggt tcg ctg caa gtc acc<br>Arg Phe Arg Glu Lys Phe Thr Gly Asp Arg Gly Ser Leu Gln Val Thr<br>370 375 380 | | 1152 |
| tgg ata cac gca ggc ggg caa gct gct tcc aga aaa ccg tcg gac acg<br>Trp Ile His Ala Gly Gly Gln Ala Ala Ser Arg Lys Pro Ser Asp Thr<br>385 390 395 400 | | 1200 |
| gca ttc ttt tgg cgc agc ggc gtt ttc cac aca tac att aca gtg cag<br>Ala Phe Phe Trp Arg Ser Gly Val Phe His Thr Tyr Ile Thr Val Gln<br>405 410 415 | | 1248 |

-continued

```
tgc ttt gag aag ttt ctg gtg gag gag atg gga gag ttc ctc cac gac    1296
Cys Phe Glu Lys Phe Leu Val Glu Glu Met Gly Glu Phe Leu His Asp
        420                 425                 430 ttc aag aag cag ctg cgg ccg tat tct cta gag gga aaa gct gcc ttt    1344
Phe Lys Lys Gln Leu Arg Pro Tyr Ser Leu Glu Gly Lys Ala Ala Phe
    435                 440                 445 atc aac ttt gcg gac agg gca ctg cca tgc gat cag cac gag gag gca    1392
Ile Asn Phe Ala Asp Arg Ala Leu Pro Cys Asp Gln His Glu Glu Ala
450                 455                 460 tac ttt ggt gat aac agg gca gag ttg cag gcg gtg aag cag att tgg    1440
Tyr Phe Gly Asp Asn Arg Ala Glu Leu Gln Ala Val Lys Gln Ile Trp
465                 470                 475                 480 gat cga tcc aag tat ttc aga tgg ggg caa ggg gtt cgt                1479
Asp Arg Ser Lys Tyr Phe Arg Trp Gly Gln Gly Val Arg
                485                 490
```

<210> SEQ ID NO 10
<211> LENGTH: 493
<212> TYPE: PRT
<213> ORGANISM: Trichoderma reesei

<400> SEQUENCE: 10

```
Met Arg Glu Leu Ile Gln Thr Leu Lys Glu Asn Lys Ile Pro Val Phe
1               5                   10                  15

Ala Pro Gly Glu Pro Gln Tyr Glu Arg Ser Val Ala Thr Val Asn Leu
            20                  25                  30

Phe Tyr Arg Phe Ala Arg Pro Asp Cys Val Val Gln Pro Arg Asn Ala
        35                  40                  45

Ser Asp Val Gln Ala Val Val Arg Glu Ala Arg Thr Arg Arg Ile His
    50                  55                  60

Ile Thr Ile Lys Asn Gly Gly His Ser Tyr Ser Gly Ala Ser Thr Ala
65                  70                  75                  80

Glu Lys Gly Ile Ser Leu Asp Leu Met Gln Met Asn Gly Val Thr Leu
                85                  90                  95

Asn Met Lys Thr Lys Leu Ala Thr Val Lys Gly Gly Ala Gln Trp Gly
            100                 105                 110

His Val Tyr Lys Gln Phe Val Ile Arg Lys Ile Asp Gly Tyr Val Val
        115                 120                 125

Asn Gly Gly Arg Cys Pro Thr Val Gly Val Ser Gly Phe Thr Leu Gly
    130                 135                 140

Gly Gly Leu Ser Pro Phe Thr Arg Ser Phe Gly Met Gly Cys Asp Ser
145                 150                 155                 160

Leu Glu Glu Ala Thr Ile Val Thr Ala Ser Gly Asp Lys Val Lys Val
                165                 170                 175

Lys Arg Ser Asp Asp Pro Arg Ser Asp Lys Gly Arg Leu Phe Trp Ala
            180                 185                 190

Leu Cys Gly Ala Gly Gly Gly Asn Phe Gly Val Val Glu Met Lys
        195                 200                 205

Leu Arg Ile Glu Lys Leu Gln Gly Asn Lys Val Val Ala Gly Arg Tyr
    210                 215                 220

Thr Trp His Pro Asp Phe Gly Pro Ser His His Pro Arg Arg Ser Ala
225                 230                 235                 240

Asp Tyr Ala Ala Thr Met Thr Gln Phe Tyr Thr Ala Asp Phe Pro Thr
                245                 250                 255

Glu Leu Thr Ile Asp Ser Thr Trp Leu Cys Asp Leu Gln Glu Ser Arg
            260                 265                 270
```

```
Asp Ala Ile Arg Phe Leu Val Tyr His Asn Gly Gly Lys Ala Glu Phe
            275                 280                 285

Asp Lys Val Ile Asp Asp Thr Ile Ser Ser Val Pro Leu Ala Thr Gln
            290                 295                 300

Leu Lys Arg Arg Ser Leu Glu Glu Ser Ser Cys Arg Phe Leu His Glu
305                 310                 315                 320

Thr Leu Val Thr Gln Trp Ser Glu Glu Ile Glu Lys Ser Leu Pro Leu
                325                 330                 335

Asn Leu Ser Phe Asn Asn Tyr Ala Ser Phe Val Phe Glu Asn Asp Arg
            340                 345                 350

Arg Asp Val Val Glu Asn Ile Ser Arg Ile Ile Arg His Asn Met Val
            355                 360                 365

Arg Phe Arg Glu Lys Phe Thr Gly Asp Arg Gly Ser Leu Gln Val Thr
            370                 375                 380

Trp Ile His Ala Gly Gly Gln Ala Ala Ser Arg Lys Pro Ser Asp Thr
385                 390                 395                 400

Ala Phe Phe Trp Arg Ser Gly Val Phe His Thr Tyr Ile Thr Val Gln
                405                 410                 415

Cys Phe Glu Lys Phe Leu Val Glu Glu Met Gly Glu Phe Leu His Asp
            420                 425                 430

Phe Lys Lys Gln Leu Arg Pro Tyr Ser Leu Glu Gly Lys Ala Ala Phe
            435                 440                 445

Ile Asn Phe Ala Asp Arg Ala Leu Pro Cys Asp Gln His Glu Glu Ala
            450                 455                 460

Tyr Phe Gly Asp Asn Arg Ala Glu Leu Gln Ala Val Lys Gln Ile Trp
465                 470                 475                 480

Asp Arg Ser Lys Tyr Phe Arg Trp Gly Gln Gly Val Arg
                485                 490

<210> SEQ ID NO 11
<211> LENGTH: 1509
<212> TYPE: DNA
<213> ORGANISM: Trichoderma reesei
<220> FEATURE:
<221> NAME/KEY: CDS
<222> LOCATION: (1)..(1509)

<400> SEQUENCE: 11 atg cgg gag att gtc act ctc cag ctg ggc aac ctc agc aac tac gtc        48
Met Arg Glu Ile Val Thr Leu Gln Leu Gly Asn Leu Ser Asn Tyr Val
1               5                   10                  15 gcc act cac ttc tgg aac gct caa gag tcc tac ttc acc tac gcc gag        96
Ala Thr His Phe Trp Asn Ala Gln Glu Ser Tyr Phe Thr Tyr Ala Glu
                20                  25                  30 gac gaa acc tca ctc gtt gat cac aac att cac tgg cgg ccg ggc att       144
Asp Glu Thr Ser Leu Val Asp His Asn Ile His Trp Arg Pro Gly Ile
            35                  40                  45 ggc gag gat gga tcg gag acg ttt ctg ccg cgg gcg gtc gtg tat gat       192
Gly Glu Asp Gly Ser Glu Thr Phe Leu Pro Arg Ala Val Val Tyr Asp
        50                  55                  60 cta aag ggc ggc ttt ggg ccg ctg aaa aag gtc aat ccc atg tat gag       240
Leu Lys Gly Gly Phe Gly Pro Leu Lys Lys Val Asn Pro Met Tyr Glu
65                  70                  75                  80 gtt gcg ccg ggc cag gat gct gct ctg gct tct cta tgg cca ggt caa       288
Val Ala Pro Gly Gln Asp Ala Ala Leu Ala Ser Leu Trp Pro Gly Gln
                85                  90                  95 ccg gca gtc cac aga cag acc ccc cta tcg caa aac acc tac cag caa       336
```

```
                Pro Ala Val His Arg Gln Thr Pro Leu Ser Gln Asn Thr Tyr Gln Gln
                            100                 105                 110 gcc ctc gac gca ggg ctc aag ccg agc gcc ctc cag gcg tca gac gtg        384
Ala Leu Asp Ala Gly Leu Lys Pro Ser Ala Leu Gln Ala Ser Asp Val
            115                 120                 125 cgc tac tgg tcc gac tac tcg cgc gtc tac tac cac ccc aaa tcc ctg        432
Arg Tyr Trp Ser Asp Tyr Ser Arg Val Tyr Tyr His Pro Lys Ser Leu
130                 135                 140 gtg cag ctg tac gac ttt gag ctc aac tcg agc atc atg ccg ttt gag        480
Val Gln Leu Tyr Asp Phe Glu Leu Asn Ser Ser Ile Met Pro Phe Glu
145                 150                 155                 160 cgc ttc gag acg ggc gcg gag ctc ttc gag tcg ctc gac aag gag gac        528
Arg Phe Glu Thr Gly Ala Glu Leu Phe Glu Ser Leu Asp Lys Glu Asp
                165                 170                 175 gag att gtc gac cgc gac tgg cgg ccc ttt gtg gag gag tgc gac cag        576
Glu Ile Val Asp Arg Asp Trp Arg Pro Phe Val Glu Glu Cys Asp Gln
            180                 185                 190 atg caa ggc gtg cag gtg tac gcc tcg ctc gac gac gcc tgg ggc ggc        624
Met Gln Gly Val Gln Val Tyr Ala Ser Leu Asp Asp Ala Trp Gly Gly
        195                 200                 205 ttc gcg agc tcc tat att gag cgg ctg cgg gac gag cat ccc aag acg        672
Phe Ala Ser Ser Tyr Ile Glu Arg Leu Arg Asp Glu His Pro Lys Thr
    210                 215                 220 tgc gtc tgg gtc tgg ggc gtg cag agc ccc gtc gcg ggc gtc ccg agg        720
Cys Val Trp Val Trp Gly Val Gln Ser Pro Val Ala Gly Val Pro Arg
225                 230                 235                 240 gag aag agg agg gtg agg ctg gcc aac acg gcg ctg agc ctc aac tcg        768
Glu Lys Arg Arg Val Arg Leu Ala Asn Thr Ala Leu Ser Leu Asn Ser
                245                 250                 255 gcg tgc gcg cag gcg tcc atg gtg gtg ccg ctg ggc gtg cct gat ggt        816
Ala Cys Ala Gln Ala Ser Met Val Val Pro Leu Gly Val Pro Asp Gly
            260                 265                 270 gcg cgg gct gtt ccg gcg agc ata gcc gtc gat agc gcc tcg ccg tgg        864
Ala Arg Ala Val Pro Ala Ser Ile Ala Val Asp Ser Ala Ser Pro Trp
        275                 280                 285 cat gtc tcc gcg ctg ctg gcg acg gct acg gag agc gcg tcg ttg cag        912
His Val Ser Ala Leu Leu Ala Thr Ala Thr Glu Ser Ala Ser Leu Gln
    290                 295                 300 tcc agg cta cgg ctc ggc ggc ggg tcg tcg cgg ccg ttg ggg ctg tct        960
Ser Arg Leu Arg Leu Gly Gly Gly Ser Ser Arg Pro Leu Gly Leu Ser
305                 310                 315                 320 gat atg gcc gag tgt ctg aac gtt tct ggc cgg cag act ctt gcc aac       1008
Asp Met Ala Glu Cys Leu Asn Val Ser Gly Arg Gln Thr Leu Ala Asn
                325                 330                 335 atg agg atg ggc gtt ggg ccg cac gcc gtc gac gcc ggg gag cgg ccg       1056
Met Arg Met Gly Val Gly Pro His Ala Val Asp Ala Gly Glu Arg Pro
            340                 345                 350 gag atg gac ttg tcg caa att ggg agc ttg aag gat ggc gct ggc agg       1104
Glu Met Asp Leu Ser Gln Ile Gly Ser Leu Lys Asp Gly Ala Gly Arg
        355                 360                 365 ctg ggg agc agc ggc ggc agt gag cgg gcc ttt ggc cgg ctg tcg           1152
Leu Gly Ser Ser Gly Gly Ser Glu Arg Ala Phe Gly Arg Leu Ser
    370                 375                 380 tct gtt cgc agg ccg gag ggg gcg aga gac gag tcg ggg gat gtg acg       1200
Ser Val Arg Arg Pro Glu Gly Ala Arg Asp Glu Ser Gly Asp Val Thr
385                 390                 395                 400 atg acg gaa cag cgt ccc att atc gga agc tca gtt gtt cga aac cat       1248
Met Thr Glu Gln Arg Pro Ile Ile Gly Ser Ser Val Val Arg Asn His
                405                 410                 415
```

```
caa aca ccc cta tta tac ccc ctc ctc gac agc ttc ccc tca ata tac    1296
Gln Thr Pro Leu Leu Tyr Pro Leu Leu Asp Ser Phe Pro Ser Ile Tyr
            420             425             430 aac tac gac ctc caa ggc cgc gag agc atc ccc gtg cac acc acc ctg    1344
Asn Tyr Asp Leu Gln Gly Arg Glu Ser Ile Pro Val His Thr Thr Leu
        435             440             445 acg tcg gac ggc tcc atc gtg cac agg atg agg aac ctg cgc acc cag    1392
Thr Ser Asp Gly Ser Ile Val His Arg Met Arg Asn Leu Arg Thr Gln
450             455             460 gtt gcg ccg tcc att tcg ctc gag gag cgg gag aac ttg gtc aac ggc    1440
Val Ala Pro Ser Ile Ser Leu Glu Glu Arg Glu Asn Leu Val Asn Gly
465             470             475             480 ttg gcg gag ctg ggg gct gcg tat gag gat gag tgg tcg agc ggg agt    1488
Leu Ala Glu Leu Gly Ala Ala Tyr Glu Asp Glu Trp Ser Ser Gly Ser
            485             490             495 gat tcg ggg gat gac gat ctc                                         1509
Asp Ser Gly Asp Asp Asp Leu
            500

<210> SEQ ID NO 12
<211> LENGTH: 503
<212> TYPE: PRT
<213> ORGANISM: Trichoderma reesei

<400> SEQUENCE: 12

Met Arg Glu Ile Val Thr Leu Gln Leu Gly Asn Leu Ser Asn Tyr Val
1               5                   10                  15

Ala Thr His Phe Trp Asn Ala Gln Glu Ser Tyr Phe Thr Tyr Ala Glu
            20                  25                  30

Asp Glu Thr Ser Leu Val Asp His Asn Ile His Trp Arg Pro Gly Ile
        35                  40                  45

Gly Glu Asp Gly Ser Glu Thr Phe Leu Pro Arg Ala Val Val Tyr Asp
    50                  55                  60

Leu Lys Gly Gly Phe Gly Pro Leu Lys Lys Val Asn Pro Met Tyr Glu
65                  70                  75                  80

Val Ala Pro Gly Gln Asp Ala Ala Leu Ala Ser Leu Trp Pro Gly Gln
                85                  90                  95

Pro Ala Val His Arg Gln Thr Pro Leu Ser Gln Asn Thr Tyr Gln Gln
            100                 105                 110

Ala Leu Asp Ala Gly Leu Lys Pro Ser Ala Leu Gln Ala Ser Asp Val
        115                 120                 125

Arg Tyr Trp Ser Asp Tyr Ser Arg Val Tyr Tyr His Pro Lys Ser Leu
    130                 135                 140

Val Gln Leu Tyr Asp Phe Glu Leu Asn Ser Ser Ile Met Pro Phe Glu
145                 150                 155                 160

Arg Phe Glu Thr Gly Ala Glu Leu Phe Glu Ser Leu Asp Lys Glu Asp
                165                 170                 175

Glu Ile Val Asp Arg Asp Trp Arg Pro Phe Val Glu Glu Cys Asp Gln
            180                 185                 190

Met Gln Gly Val Gln Val Tyr Ala Ser Leu Asp Asp Ala Trp Gly Gly
        195                 200                 205

Phe Ala Ser Ser Tyr Ile Glu Arg Leu Arg Asp Glu His Pro Lys Thr
    210                 215                 220

Cys Val Trp Val Trp Gly Val Gln Ser Pro Val Ala Gly Val Pro Arg
225                 230                 235                 240

Glu Lys Arg Arg Val Arg Leu Ala Asn Thr Ala Leu Ser Leu Asn Ser
                245                 250                 255
```

```
Ala Cys Ala Gln Ala Ser Met Val Val Pro Leu Gly Val Pro Asp Gly
                260                 265                 270

Ala Arg Ala Val Pro Ala Ser Ile Ala Val Asp Ser Ala Ser Pro Trp
            275                 280                 285

His Val Ser Ala Leu Leu Ala Thr Ala Thr Glu Ser Ala Ser Leu Gln
        290                 295                 300

Ser Arg Leu Arg Leu Gly Gly Gly Ser Ser Arg Pro Leu Gly Leu Ser
305                 310                 315                 320

Asp Met Ala Glu Cys Leu Asn Val Ser Gly Arg Gln Thr Leu Ala Asn
                325                 330                 335

Met Arg Met Gly Val Gly Pro His Ala Val Asp Ala Gly Glu Arg Pro
            340                 345                 350

Glu Met Asp Leu Ser Gln Ile Gly Ser Leu Lys Asp Gly Ala Gly Arg
        355                 360                 365

Leu Gly Ser Ser Gly Gly Gly Ser Glu Arg Ala Phe Gly Arg Leu Ser
    370                 375                 380

Ser Val Arg Arg Pro Glu Gly Ala Arg Asp Glu Ser Gly Asp Val Thr
385                 390                 395                 400

Met Thr Glu Gln Arg Pro Ile Ile Gly Ser Ser Val Val Arg Asn His
                405                 410                 415

Gln Thr Pro Leu Leu Tyr Pro Leu Leu Asp Ser Phe Pro Ser Ile Tyr
            420                 425                 430

Asn Tyr Asp Leu Gln Gly Arg Glu Ser Ile Pro Val His Thr Thr Leu
        435                 440                 445

Thr Ser Asp Gly Ser Ile Val His Arg Met Arg Asn Leu Arg Thr Gln
    450                 455                 460

Val Ala Pro Ser Ile Ser Leu Glu Glu Arg Glu Asn Leu Val Asn Gly
465                 470                 475                 480

Leu Ala Glu Leu Gly Ala Ala Tyr Glu Asp Glu Trp Ser Ser Gly Ser
                485                 490                 495

Asp Ser Gly Asp Asp Asp Leu
            500

<210> SEQ ID NO 13
<211> LENGTH: 2172
<212> TYPE: DNA
<213> ORGANISM: Trichoderma reesei
<220> FEATURE:
<221> NAME/KEY: CDS
<222> LOCATION: (1)..(2172)

<400> SEQUENCE: 13 atg aga gac ctt ctc cag gag cta gtg aaa aga ctg gct cag gag ctg    48
Met Arg Asp Leu Leu Gln Glu Leu Val Lys Arg Leu Ala Gln Glu Leu
1               5                   10                  15 gga cca caa gaa agg cgg tgc cta caa gat cta cat atc acc gat cct    96
Gly Pro Gln Glu Arg Arg Cys Leu Gln Asp Leu His Ile Thr Asp Pro
            20                  25                  30 cgt ctt gat aga gat cga atc ata tcg acc aaa gga ggg cta ttg caa    144
Arg Leu Asp Arg Asp Arg Ile Ile Ser Thr Lys Gly Gly Leu Leu Gln
        35                  40                  45 gct tca tat cag tgg atc ctc gag gac tct act gta cgc cat tgg cgt    192
Ala Ser Tyr Gln Trp Ile Leu Glu Asp Ser Thr Val Arg His Trp Arg
    50                  55                  60 caa gag cgg cag aaa agt ctt ctc tgg atc aag ggc gac cca ggc aaa    240
Gln Glu Arg Gln Lys Ser Leu Leu Trp Ile Lys Gly Asp Pro Gly Lys
65                  70                  75                  80
```

-continued

| | | |
|---|---|---|
| ggc aag acg atg atg ctt tgc ggc ctc agt cag gaa ttg gaa gat gca<br>Gly Lys Thr Met Met Leu Cys Gly Leu Ser Gln Glu Leu Glu Asp Ala<br>               85                               90                    95 | 288 |
| aga gaa ggc cca tcc ctc ttg tct tac ttc ttc tgt cag gct aca gtc<br>Arg Glu Gly Pro Ser Leu Leu Ser Tyr Phe Phe Cys Gln Ala Thr Val<br>              100                      105                     110 | 336 |
| cca act ttg aat aca gcc act gct gtg ttg agg ggg ctt tta tac ctg<br>Pro Thr Leu Asn Thr Ala Thr Ala Val Leu Arg Gly Leu Leu Tyr Leu<br>         115                       120                    125 | 384 |
| cta gtg att cga cac cca tcg ctt ttc cct cac ttg cag gac gcc tat<br>Leu Val Ile Arg His Pro Ser Leu Phe Pro His Leu Gln Asp Ala Tyr<br>130                       135                    140 | 432 |
| gag aag gtc ggc gat cga aag ctc ttt gag gga gtg aac agc tgg ttt<br>Glu Lys Val Gly Asp Arg Lys Leu Phe Glu Gly Val Asn Ser Trp Phe<br>145                       150                    155                    160 | 480 |
| gcc ttg atc aaa atc ttc aac aag atg atg aaa gat cag cta ttg caa<br>Ala Leu Ile Lys Ile Phe Asn Lys Met Met Lys Asp Gln Leu Leu Gln<br>              165                      170                    175 | 528 |
| aat tca tgc ttc atc atc gac gct ctc gac gag tgc tcc gat cgc gac<br>Asn Ser Cys Phe Ile Ile Asp Ala Leu Asp Glu Cys Ser Asp Arg Asp<br>         180                       185                    190 | 576 |
| aag ctc ttg gat ctc atc gtc gat agc tgt gct agt acg ccc ggt gtc<br>Lys Leu Leu Asp Leu Ile Val Asp Ser Cys Ala Ser Thr Pro Gly Val<br>             195                      200                    205 | 624 |
| aaa tgg atc ttg tca agt cgg aaa ctt cga gat att gag gcc aaa ttt<br>Lys Trp Ile Leu Ser Ser Arg Lys Leu Arg Asp Ile Glu Ala Lys Phe<br>         210                       215                    220 | 672 |
| gga cgt tgt gaa cat agc gtc gtg gtt gac ctt gaa gag cac aac gac<br>Gly Arg Cys Glu His Ser Val Val Val Asp Leu Glu Glu His Asn Asp<br>225                       230                    235                    240 | 720 |
| tcg act att gat agt gtc aag aag ttc atc ggc agt cga ctt cag aag<br>Ser Thr Ile Asp Ser Val Lys Lys Phe Ile Gly Ser Arg Leu Gln Lys<br>             245                      250                    255 | 768 |
| ctg gag ctt gtt gag gac aat ccg aac ctc caa gaa aaa ctc cga gac<br>Leu Glu Leu Val Glu Asp Asn Pro Asn Leu Gln Glu Lys Leu Arg Asp<br>             260                      265                    270 | 816 |
| atc att cta cag aag tcc aat cga aca ttt ctc tgg gct gct ttg gtc<br>Ile Ile Leu Gln Lys Ser Asn Arg Thr Phe Leu Trp Ala Ala Leu Val<br>         275                      280                    285 | 864 |
| att gag gag ctc aag aat ctt gaa aca tac gag gaa gag agc gaa gtg<br>Ile Glu Glu Leu Lys Asn Leu Glu Thr Tyr Glu Glu Glu Ser Glu Val<br>         290                      295                    300 | 912 |
| ttg cag ttt ctg gat aaa atg ccc agc ggt ctg cct gaa cta tat gac<br>Leu Gln Phe Leu Asp Lys Met Pro Ser Gly Leu Pro Glu Leu Tyr Asp<br>305                       310                    315                    320 | 960 |
| aga atg att gcc caa atc aga cag atg gga agc aaa ctg gat cgg gat<br>Arg Met Ile Ala Gln Ile Arg Gln Met Gly Ser Lys Leu Asp Arg Asp<br>             325                      330                    335 | 1008 |
| cgg tgc ttt agg att cta tcg act atg gct acc acc tat cgc ccc ctc<br>Arg Cys Phe Arg Ile Leu Ser Thr Met Ala Thr Thr Tyr Arg Pro Leu<br>         340                      345                    350 | 1056 |
| aat ctg aca gcg cta ccc ctc cta gct gat ttg aag gga aat ctt gcc<br>Asn Leu Thr Ala Leu Pro Leu Leu Ala Asp Leu Lys Gly Asn Leu Ala<br>             355                      360                    365 | 1104 |
| aag cca gag aca ctg agg aag ttg att caa atg tgt ggc tct ttc ttg<br>Lys Pro Glu Thr Leu Arg Lys Leu Ile Gln Met Cys Gly Ser Phe Leu<br>370                       375                    380 | 1152 |
| acc att caa gat cag acg atc tac ttc att cac caa tcg gcc aag gac<br>Thr Ile Gln Asp Gln Thr Ile Tyr Phe Ile His Gln Ser Ala Lys Asp | 1200 |

-continued

| | | | | |
|---|---|---|---|---|
| 385 | 390 | 395 | 400 | |
| tat ttg gtt caa aca gga aat cac gtc atc cat cat aac ata tat cac<br>Tyr Leu Val Gln Thr Gly Asn His Val Ile His His Asn Ile Tyr His<br>405 410 415 | | | | 1248 |
| cgg tct gtc gaa gtg ctg aag tcg caa gga ggc ttg agg gca aac ata<br>Arg Ser Val Glu Val Leu Lys Ser Gln Gly Gly Leu Arg Ala Asn Ile<br>420 425 430 | | | | 1296 |
| tac ggc ttg acc tat ccc ggt gcc aag att gag gaa atc tcc ccg cct<br>Tyr Gly Leu Thr Tyr Pro Gly Ala Lys Ile Glu Glu Ile Ser Pro Pro<br>435 440 445 | | | | 1344 |
| caa ccg gat cct ctt gag cat ata cag tac tgc tgc gtg tac tgg ctt<br>Gln Pro Asp Pro Leu Glu His Ile Gln Tyr Cys Cys Val Tyr Trp Leu<br>450 455 460 | | | | 1392 |
| caa cac ttc tgc gat agc ctc gaa gct atc aga gcc cct gaa acc aag<br>Gln His Phe Cys Asp Ser Leu Glu Ala Ile Arg Ala Pro Glu Thr Lys<br>465 470 475 480 | | | | 1440 |
| gtc gtt gag aag gtc ttt acg ttc tta caa cag cat cta ttg cat tgg<br>Val Val Glu Lys Val Phe Thr Phe Leu Gln Gln His Leu Leu His Trp<br>485 490 495 | | | | 1488 |
| ttc gaa gcc ttg agt ctc ctc aag agt cta cag gcg ggc atc tta tcg<br>Phe Glu Ala Leu Ser Leu Leu Lys Ser Leu Gln Ala Gly Ile Leu Ser<br>500 505 510 | | | | 1536 |
| ttg cag aga cta ctt acg ctc tcc acc gga agt gat cgc ttc tca aac<br>Leu Gln Arg Leu Leu Thr Leu Ser Thr Gly Ser Asp Arg Phe Ser Asn<br>515 520 525 | | | | 1584 |
| ttc ttc caa gac gct tgc cgc ttc tgc atc cat aac aga tat atc atc<br>Phe Phe Gln Asp Ala Cys Arg Phe Cys Ile His Asn Arg Tyr Ile Ile<br>530 535 540 | | | | 1632 |
| gaa acc gct cca ctt cag gtt tac gtt tcc gcg ctc atc ttc agt ccg<br>Glu Thr Ala Pro Leu Gln Val Tyr Val Ser Ala Leu Ile Phe Ser Pro<br>545 550 555 560 | | | | 1680 |
| cgt cag agt gag ata cgg cag cat ttc caa agc gcg ctg tct tgg atc<br>Arg Gln Ser Glu Ile Arg Gln His Phe Gln Ser Ala Leu Ser Trp Ile<br>565 570 575 | | | | 1728 |
| aag ctg tta cct gat gtt ggt gac gat tgg gac tca tgt ctg ttc acc<br>Lys Leu Leu Pro Asp Val Gly Asp Asp Trp Asp Ser Cys Leu Phe Thr<br>580 585 590 | | | | 1776 |
| cta gaa ggt cat gaa tct agg gtc gtg tgt gtg gct ttc tca gac gac<br>Leu Glu Gly His Glu Ser Arg Val Val Cys Val Ala Phe Ser Asp Asp<br>595 600 605 | | | | 1824 |
| tct aga ttc ttg gct tcg tca gct ggc gat ggg act gtc cga gtt tgg<br>Ser Arg Phe Leu Ala Ser Ser Ala Gly Asp Gly Thr Val Arg Val Trp<br>610 615 620 | | | | 1872 |
| gat cca act act gga gac gcc att cat gcc ttt cca ata atg gta gaa<br>Asp Pro Thr Thr Gly Asp Ala Ile His Ala Phe Pro Ile Met Val Glu<br>625 630 635 640 | | | | 1920 |
| tcc gat gat gca atc ctg atg cct aac aca tat tac aat gtc ggg ccg<br>Ser Asp Asp Ala Ile Leu Met Pro Asn Thr Tyr Tyr Asn Val Gly Pro<br>645 650 655 | | | | 1968 |
| gtt gct ttt tct cat gac tct aag ctt gta tcc ttt ggc tat aaa gat<br>Val Ala Phe Ser His Asp Ser Lys Leu Val Ser Phe Gly Tyr Lys Asp<br>660 665 670 | | | | 2016 |
| ggc agc gta cga gtc tgg gat ttg gag gat gga atc gaa cta caa ctg<br>Gly Ser Val Arg Val Trp Asp Leu Glu Asp Gly Ile Glu Leu Gln Leu<br>675 680 685 | | | | 2064 |
| cat act gga cat ata gag ccc gtg aat tgg gtg gcc ttc tcg aag gat<br>His Thr Gly His Ile Glu Pro Val Asn Trp Val Ala Phe Ser Lys Asp<br>690 695 700 | | | | 2112 |
| tcc agg ttt cta gcc aca gct tcg aat gat tgg acg gtt aaa cta tgg<br> | | | | 2160 |

```
Ser Arg Phe Leu Ala Thr Ala Ser Asn Asp Trp Thr Val Lys Leu Trp
705                 710                 715                 720 acg aca acc acg                                                      2172
Thr Thr Thr Thr
```

<210> SEQ ID NO 14
<211> LENGTH: 724
<212> TYPE: PRT
<213> ORGANISM: Trichoderma reesei

<400> SEQUENCE: 14

```
Met Arg Asp Leu Leu Gln Glu Leu Val Lys Arg Leu Ala Gln Glu Leu
1               5                   10                  15

Gly Pro Gln Glu Arg Arg Cys Leu Gln Asp Leu His Ile Thr Asp Pro
            20                  25                  30

Arg Leu Asp Arg Asp Arg Ile Ile Ser Thr Lys Gly Gly Leu Leu Gln
        35                  40                  45

Ala Ser Tyr Gln Trp Ile Leu Glu Asp Ser Thr Val Arg His Trp Arg
    50                  55                  60

Gln Glu Arg Gln Lys Ser Leu Leu Trp Ile Lys Gly Asp Pro Gly Lys
65                  70                  75                  80

Gly Lys Thr Met Met Leu Cys Gly Leu Ser Gln Glu Leu Glu Asp Ala
                85                  90                  95

Arg Glu Gly Pro Ser Leu Leu Ser Tyr Phe Phe Cys Gln Ala Thr Val
            100                 105                 110

Pro Thr Leu Asn Thr Ala Thr Ala Val Leu Arg Gly Leu Leu Tyr Leu
        115                 120                 125

Leu Val Ile Arg His Pro Ser Leu Phe Pro His Leu Gln Asp Ala Tyr
    130                 135                 140

Glu Lys Val Gly Asp Arg Lys Leu Phe Glu Gly Val Asn Ser Trp Phe
145                 150                 155                 160

Ala Leu Ile Lys Ile Phe Asn Lys Met Met Lys Asp Gln Leu Leu Gln
                165                 170                 175

Asn Ser Cys Phe Ile Ile Asp Ala Leu Asp Glu Cys Ser Asp Arg Asp
            180                 185                 190

Lys Leu Leu Asp Leu Ile Val Asp Ser Cys Ala Ser Thr Pro Gly Val
        195                 200                 205

Lys Trp Ile Leu Ser Ser Arg Lys Leu Arg Asp Ile Glu Ala Lys Phe
    210                 215                 220

Gly Arg Cys Glu His Ser Val Val Val Asp Leu Glu Glu His Asn Asp
225                 230                 235                 240

Ser Thr Ile Asp Ser Val Lys Lys Phe Ile Gly Ser Arg Leu Gln Lys
                245                 250                 255

Leu Glu Leu Val Glu Asp Asn Pro Leu Gln Glu Lys Leu Arg Asp
            260                 265                 270

Ile Ile Leu Gln Lys Ser Asn Arg Thr Phe Leu Trp Ala Ala Leu Val
        275                 280                 285

Ile Glu Glu Leu Lys Asn Leu Glu Thr Tyr Glu Glu Ser Glu Val
    290                 295                 300

Leu Gln Phe Leu Asp Lys Met Pro Ser Gly Leu Pro Glu Leu Tyr Asp
305                 310                 315                 320

Arg Met Ile Ala Gln Ile Arg Gln Met Gly Ser Lys Leu Asp Arg Asp
                325                 330                 335

Arg Cys Phe Arg Ile Leu Ser Thr Met Ala Thr Thr Tyr Arg Pro Leu
            340                 345                 350
```

Asn Leu Thr Ala Leu Pro Leu Ala Asp Leu Lys Gly Asn Leu Ala
        355                 360                 365

Lys Pro Glu Thr Leu Arg Lys Leu Ile Gln Met Cys Gly Ser Phe Leu
    370                 375                 380

Thr Ile Gln Asp Gln Thr Ile Tyr Phe Ile His Gln Ser Ala Lys Asp
385                 390                 395                 400

Tyr Leu Val Gln Thr Gly Asn His Val Ile His Asn Ile Tyr His
                405                 410                 415

Arg Ser Val Glu Val Leu Lys Ser Gln Gly Gly Leu Arg Ala Asn Ile
                420                 425                 430

Tyr Gly Leu Thr Tyr Pro Gly Ala Lys Ile Glu Glu Ile Ser Pro Pro
            435                 440                 445

Gln Pro Asp Pro Leu Glu His Ile Gln Tyr Cys Cys Val Tyr Trp Leu
        450                 455                 460

Gln His Phe Cys Asp Ser Leu Glu Ala Ile Arg Ala Pro Glu Thr Lys
465                 470                 475                 480

Val Val Glu Lys Val Phe Thr Phe Leu Gln Gln His Leu Leu His Trp
                485                 490                 495

Phe Glu Ala Leu Ser Leu Leu Lys Ser Leu Gln Ala Gly Ile Leu Ser
                500                 505                 510

Leu Gln Arg Leu Leu Thr Leu Ser Thr Gly Ser Asp Arg Phe Ser Asn
            515                 520                 525

Phe Phe Gln Asp Ala Cys Arg Phe Cys Ile His Asn Arg Tyr Ile Ile
        530                 535                 540

Glu Thr Ala Pro Leu Gln Val Tyr Val Ser Ala Leu Ile Phe Ser Pro
545                 550                 555                 560

Arg Gln Ser Glu Ile Arg Gln His Phe Gln Ser Ala Leu Ser Trp Ile
                565                 570                 575

Lys Leu Leu Pro Asp Val Gly Asp Asp Trp Asp Ser Cys Leu Phe Thr
            580                 585                 590

Leu Glu Gly His Glu Ser Arg Val Val Cys Val Ala Phe Ser Asp Asp
            595                 600                 605

Ser Arg Phe Leu Ala Ser Ala Gly Asp Gly Thr Val Arg Val Trp
    610                 615                 620

Asp Pro Thr Thr Gly Asp Ala Ile His Ala Phe Pro Ile Met Val Glu
625                 630                 635                 640

Ser Asp Asp Ala Ile Leu Met Pro Asn Thr Tyr Tyr Asn Val Gly Pro
                645                 650                 655

Val Ala Phe Ser His Asp Ser Lys Leu Val Ser Phe Gly Tyr Lys Asp
                660                 665                 670

Gly Ser Val Arg Val Trp Asp Leu Glu Asp Gly Ile Glu Leu Gln Leu
            675                 680                 685

His Thr Gly His Ile Glu Pro Val Asn Trp Val Ala Phe Ser Lys Asp
        690                 695                 700

Ser Arg Phe Leu Ala Thr Ala Ser Asn Asp Trp Thr Val Lys Leu Trp
705                 710                 715                 720

Thr Thr Thr Thr

<210> SEQ ID NO 15
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 15
cgtttccagt gcgcaaagta ccgcgcgctt gacaa         35

<210> SEQ ID NO 16
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 16
ccaatgatgt gcgcatctgg gaaatgttct ttggc         35

<210> SEQ ID NO 17
<211> LENGTH: 3089
<212> TYPE: DNA
<213> ORGANISM: Aspergillus nidurans

<400> SEQUENCE: 17

| | |
|---|---|
| tgcgcacatc attggatagg cagattactc agcctgaatg acatcaacat gttacccatg | 60 |
| atacaatagg tcacacaaac aagcgctaag atgcacttgg tatgacaagc ccagtagtcc | 120 |
| gtttcaaaag acctagatga tgaactacaa catgaggtgt tgcctcctga tccagtccaa | 180 |
| ctgcaaacgc tgatgtatac tcaatcaagc ctgatgtaaa tgctgcgact cgattcgctg | 240 |
| gatatgaaga tcaaagagag ctctgatggg tccaatatag ccgggttttg ttaggacagt | 300 |
| ccaccacacc gatattagaa ttggtcaagc accttatcat ttcatagaga ttgcggtttc | 360 |
| tagatctacg ccaggaccga gcaagcccag atgagaaccg acgcagattt ccttggcacc | 420 |
| tgttgcttca gctgaatcct ggcaatacga gatacctgct ttgaatattt tgaatagctc | 480 |
| gcccgctgga gagcatcctg aatgcaagta acaaccgtag aggctgacac ggcaggtgtt | 540 |
| gctagggagc gtcgtgttct acaaggccag acgtcttcgc ggttgatata tatgtatgtt | 600 |
| tgactgcagg ctgctcagcg acgacagtca agttcgccct cgctgcttgt gcaataatcg | 660 |
| cagtggggaa gccacaccgt gactcccatc tttcagtaaa gctctgttgg tgtttatcag | 720 |
| caatacacgt aatttaaact cgttagcatg gggctgatag cttaattacc gtttaccagt | 780 |
| gccgcggttc tgcagctttc cttggcccgt aaaattcggc gaagccagcc aatcaccagc | 840 |
| taggcaccag ctaaacccta taattagtct cttatcaaca ccatccgctc ccccgggatc | 900 |
| aatgaggaga atgaggggga tgcggggcta agaagcccta cataaccctc atgccaactc | 960 |
| ccagtttaca ctcgtcgagc caacatcctg actataagct aacacagaat gcctcaatcc | 1020 |
| tgggaagaac tggccgctga taagcgcgcc cgcctcgcaa aaaccatccc tgatgaatgg | 1080 |
| aaagtccaga cgctgcctgc ggaagacagc gttattgatt tcccaaagaa atcgggggatc | 1140 |
| ctttcagagg ccgaactgaa gatcacagag gcctccgctg cagatcttgt gtccaagctg | 1200 |
| gcggccggag agttgacctc ggtggaagtt acgctagcat tctgtaaacg ggcagcaatc | 1260 |
| gcccagcagt tagtagggtc ccctctacct ctcagggaga tgtaacaacg ccaccttatg | 1320 |
| ggactatcaa gctgacgctg gcttctgtgc agacaaactg cgcccacgag ttcttccctg | 1380 |
| acgccgctct cgcgcaggca agggaactcg atgaatacta cgcaaagcac aagagacccg | 1440 |
| ttggtccact ccatggcctc cccatctctc tcaaagacca gcttcgagtc aaggtacacc | 1500 |
| gttgcccta agtcgttaga tgtccctttt tgtcagctaa catatgccac cagggctacg | 1560 |
| aaacatcaat gggctacatc tcatggctaa acaagtacga cgaaggggac tcggttctga | 1620 |

```
caaccatgct ccgcaaagcc ggtgccgtct tctacgtcaa gacctctgtc ccgcagaccc    1680
tgatggtctg cgagacagtc aacaacatca tcgggcgcac cgtcaaccca cgcaacaaga    1740
actggtcgtg cggcggcagt tctggtggtg agggtgcgat cgttgggatt cgtggtggcg    1800
tcatcggtgt aggaacggat atcggtggct cgattcgagt gccggccgcg ttcaacttcc    1860
tgtacggtct aaggccgagt catgggcggc tgccgtatgc aaagatggcg aacagcatgg    1920
agggtcagga cggtgcac   agcgttgtcg ggccgattac gcactctgtt gagggtgagt    1980
ccttcgcctc ttccttcttt tcctgctcta taccaggcct ccactgtcct cctttcttgc    2040
tttttatact atatacgaga ccggcagtca ctgatgaagt atgttagacc tccgcctctt    2100
caccaaatcc gtcctcggtc aggagccatg gaaatacgac tccaaggtca tccccatgcc    2160
ctggcgccag tccgagtcgg acattattgc ctccaagatc aagaacgcg  ggctcaatat    2220 cggctactac aacttcgacg gcaatgtcct tccacaccct cctatcctgc gcggcgtgga    2280
aaccaccgtc gccgcactcg ccaaagccgg tcacaccgtg accccgtgga cgccatacaa    2340
gcacgatttc ggccacgatc tcatctccca tatctacgcg gctgacggca gcgccgacgt    2400
aatgcgcgat atcagtgcat ccggcgagcc ggcgattcca aatatcaaag acctactgaa    2460
cccgaacatc aaagctgtta acatgaacga gctctgggac acgcatctcc agaagtggaa    2520
ttaccagatg gagtaccttg agaaatggcg ggaggctgaa gaaaaggccg ggaaggaact    2580
ggacgccatc atcgcgccga ttacgcctac cgctgcggta cggcatgacc agttccggta    2640
ctatgggtat gcctctgtga tcaacctgct ggatttcacg agcgtggttg ttccggttac    2700
ctttgcggat aagaacatcg ataagaagaa tgagagtttc aaggcggtta gtgagcttga    2760
tgccctcgtg caggaagagt atgatccgga ggcgtaccat ggggcaccgg ttgcagtgca    2820
ggttatcgga cggagactca gtgaagagag gacgttggcg attgcagagg aagtggggaa    2880
gttgctggga aatgtggtga ctccatagct aataagtgtc agatagcaat ttgcacaaga    2940
aatcaatacc agcaactgta ataagcgct  gaagtgacca tgccatgcta cgaaagagca    3000
gaaaaaaacc tgccgtagaa ccgaagagat atgacacgct tccatctctc aaaggaagaa    3060
tcccttcagg gttgcgtttc cagtgcgca                                     3089

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
tgcgcacatc attggatagg                                                20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
tgcgcactgg aaacgcaacc                                                20

<210> SEQ ID NO 20
<211> LENGTH: 3844
<212> TYPE: DNA
<213> ORGANISM: Trichoderma reesei
```

<400> SEQUENCE: 20

```
tttcgcctta gcggttccat ctgttcggta ctggcagaca tgggttcaca ttgatgtatc      60
taatagtccg ttgcatgcta ctactacaac tataaaatgt gttcatgatc gctatcatac     120
ctaaactgtc atcattataa ctacctccta tctcctgtct acttgatgaa caaaaattga     180
tgatactacc tattcacggc cattcccta agaagagccc acatgtttaa aaaagcattc      240
gtatcgggcc gctgtggata gcttcggaaa tggtagagaa aaacacgacc ccaccatata     300
tcctctcaat cccgtctgcg tccaagatat gtcgttacct agagctaggc agtagcaata     360
tgcccttgaa aattcaggtg cctaaggtac agtcggactg aatctggcaa tctgtaagca     420
aatgcacgat ccgtcactaa ggtacctacc gaatagagct ctaccttagg tttccatagg     480
tattcgggaa cagcatggcg ctcaccaaca ggcgcttctg cagcagagag cagcagccac     540
ttacaccatg aagcttcttc aaagtccaat cccgtatcga gcctcttgca tcccatgcgc     600
tattttagcg gctgttatcc gcgccatcac agcccaacga tagacagcct ggacctcgcc     660
tgccagcagc aagcagtggc acatgcaagt acctcctgtc taggtagcga gctcaacagc     720
tctgcaggga gaggaggagg gggaaaagag agaacaaagt cccctggcag ctcgattgat     780
gatccaacgt tccagaaccg ggaccccacc aaagtcgaaa atcccacccg agcgagcttt     840
ataaaatctc caccaagccg aaccatcacc agatcttccc tctgcccaaa agtgcgacaa     900
cttcttccag gaacttttc ttatttattt actctctcac tctatacagc tttactcctc      960
cattatattg ccaaagaaca tttcccagaa tgagaggcga ggtcagtgtt cccctttctt    1020
cccgcgcgag cgattctcta ggtttcgcac ttcttccatc tggtgcgatg atatcattcc    1080
acttttgcg acatggcgat gcgtcactcc cgacagagcc gttttcgca gcctctgcgc     1140
ccatctcgac gatgcgattt tctcacagga gagcgtcgct aacatgagcc tcacatagat    1200
tctgcatctg cacgtcggcc aggccggtgt tcagctcggc aacgcagctt gggagctgtt    1260
cgtgagcccc tccaccattg cttgcgcgcg cgcaaggccg attcagaagc cgccccatgt    1320
ttgctaactc tctctctctc tctctcttct tttcgcacag ctactgtctc gagcacggca    1380
tcggccgcga cggtcgcatc agcgcggacg tccaggaccc cgatgatctg ggctctcccg    1440
acaccttctt caccgagacc agcaacggca agcacgtgcc gcgggccatc ttcgtcgacc    1500
tcgacccgtc cccatcgac gagatccggg cgggcgacta ccgccagctg ttccatccgg     1560
aactgctcat cagcggcaag gaggatgcgg ccaacaacta tgcgcgcggg cactacaccg    1620
tcggcaagga gatgattgac accgtcatgg acaagatccg ccgtgtcaca ggtgagtttt    1680
ttttctgcg ctggcgagac caggacgatg ccttgtttga cgtgaagtgg tggcctgact     1740
tgtcatcgct gtaccagac aactgtcact ccctccaggg gttctcatg ttccactcct      1800
ttggcggcgg cactggctcc ggctttggtg cgctgatgct tgagcgtctg gccaccgagt    1860
acggcaagaa gacgaagctc gagttttgccg tctacccagc tcctcgcacg tcctcggccg    1920
tcgtcgagcc ttacaatgca gtcctctcga cccacagcac catcgagcac tcggactgca    1980
ccttcttggt ggacaacgag gcagtctatg acatttgcaa gcggaatctc gacatctctc    2040
ggccgtcctt cgatcacctc aaccgcctca ttgcccaagt ggtcagctcc atcacgtcgt    2100
ctctgcgatt cgacggcgcg ctcaacgtcg acctgaacga gttccagacc aacctggttc    2160
cttcccgcg catccactac cccctgatca gctacgcccc ggttgtttcc acaaagaagg    2220
cctcccacga aagcttcaag gttcaggagc tgacacttca gtgtaagcac tcaaagatcc    2280
```

-continued

```
ccaaataccc atcttgtgtg tatctccccc ccggggtact gactctgtaa ccaaggcttt    2340
gaacccaaca accagatggt cgtctgcgac ccccgcaacg gcaagtacat ggccgtggtc    2400
ctgctgtatc gcggcgacgt cgtgactcgt gactgcacag tcgccgtcgc ccacgtcaag    2460
gccaaggcaa ccttcaacat ggtcgactgg tgcccacgg gcttcaagct cggcatcacc     2520
taccagaagc ccacggccgt ccccgtcgac gctcaggagg gcggcctcgc cgccgtcaag    2580
cgctccgtgt ccatgctctc caacacgacc gccatcgccg aagcctggtc gcggctggac    2640
tataagtttg acctcatgca caacaagcgc gcatttgtcc actggtacgt cggcgagggc    2700
atggaggagg gcgagttctc ggaggcgcga gaggatctgg ctgctctgga gagggattac    2760
gcggaggttg ctgccgactc tttcgagcct gacgagactg ccgagtatta aaagtaccgc    2820
gcgcttgaca agaaatgtga ttcggccgac gacgacttga cgctgaaacg aaatggagac    2880
gaaacgagga cttgttgtga tataacggaa aggttttggc cttgagtttt tctctgacat    2940
cggtgtggtc gtattggagt ctagactgtt ccattccctc cttcgccatt cgcgcccctt    3000
tccccttgtt ttcatctgtc tgtttatttt ccctttcttt ttgcctttct tgctggatat    3060
ggatgtttgg agcaagcatg cacagaaaaa aacaccacgt tgatacctct aataccacca    3120
aagttgatat ctctttcgtt gtacatacct aatatgaatg atccttttcc ccccctaccc    3180
agtctatcat catttgattt accttttgtt gttacctgtc gtcatctaat actgaggagc    3240
cgtttgattt aagctctctt ttcgttcgtg tttcaaaacc atgcatgtac tgcttaccac    3300
cgggcattca gtcattgggc ggcagggcga gttttccgcc tccaaatgac gtggcagcct    3360
tgtggcaata ctgactgacc tgccagctca cgtctcaaac atgtagcaat ttcatatagg    3420
gatgttcgac tcttattctc aaattctttg atcccaaaat gtgcacggag atggaaagga    3480
ctcaaactgc taactgctgt cttcagcatt cacataggta ccttacatac tattacctag    3540
gtagtagtag gtaaagcgct ggcggtagga ataccctgga gttcctccta atatttaaac    3600
acatcaagta acctttatgt tcatcatcta ttcggcaaac gccattcatc tccatctcta    3660
ttgttctact atctgtatca ggtataaaaa agcagcatgt ctctgacaac tgacaagcca    3720
atgaggtaat cccaaagagg aggctcatct tcaaaggggg taggagaggg gaaggcaaag    3780
cgacaaaaag aaaaaggaac cttcaacatg tacatttact tgccccctcc aaaccaagaa    3840
ccaa                                                                3844
```